(12) United States Patent
Shibuya et al.

(10) Patent No.: US 6,406,909 B1
(45) Date of Patent: Jun. 18, 2002

(54) SERUM-FREE MEDIUM FOR CULTURING ANIMAL CELLS

(75) Inventors: Kazushi Shibuya; Masaru Atsumi; Shigeyuki Tsunakawa; Kaneo Nogaki, all of Tokyo (JP); Thomas Reid Fletcher, Costa Mesa, CA (US); Katsuyuki Imada, Tokyo (JP); Bjorn Kenneth Lydersen, Encinitas, CA (US)

(73) Assignees: Chugai Seiyaku Kabushiki Kaisha, Tokyo (JP); Irvine Scientific Sales Company, Santa Ana, CA (US)

( * ) Notice: Subject to any disclaimer, the term of this patent is extended or adjusted under 35 U.S.C. 154(b) by 0 days.

(21) Appl. No.: 09/113,357

(22) Filed: Jul. 10, 1998

(51) Int. Cl.$^7$ .................................................. C12N 5/06
(52) U.S. Cl. ...................... 435/404; 435/69.1; 435/383; 435/391
(58) Field of Search ................................ 435/383, 69.1, 435/404, 240, 391

(56) References Cited

U.S. PATENT DOCUMENTS 5,633,162 A    5/1997   Keen et al. .................. 435/384

FOREIGN PATENT DOCUMENTS

| EP | 0 481 791 | * | 4/1992 | ............. C12N/5/02 |
|----|-----------|---|--------|------------------------|
| JP | 02049579  | * | 2/1990 |                        |
| WO | WO 98/08934 |  | 3/1998 |                        |
| WO | WO 98/15614 |  | 4/1998 |                        |

OTHER PUBLICATIONS

Patent Abstracts of Japan, vol. 0142, No. 15, May 8, 1990.

* cited by examiner

*Primary Examiner*—Jean C. Witz
(74) *Attorney, Agent, or Firm*—Foley & Lardner

(57) ABSTRACT

The present invention relates to a serum-free medium for culturing animal cells which contains soybean protein hydrolysate and yeast extract; a method for culturing animal cells which comprises a step of culturing animal cells in the serum-free medium; and a method for producing a desired substance which comprises a step of culturing animal cells in the serum-free medium, causing the desired substance to be produced by and secreted out of the animal cells and a step of isolating the desired substance from the serum-free medium.

20 Claims, 13 Drawing Sheets

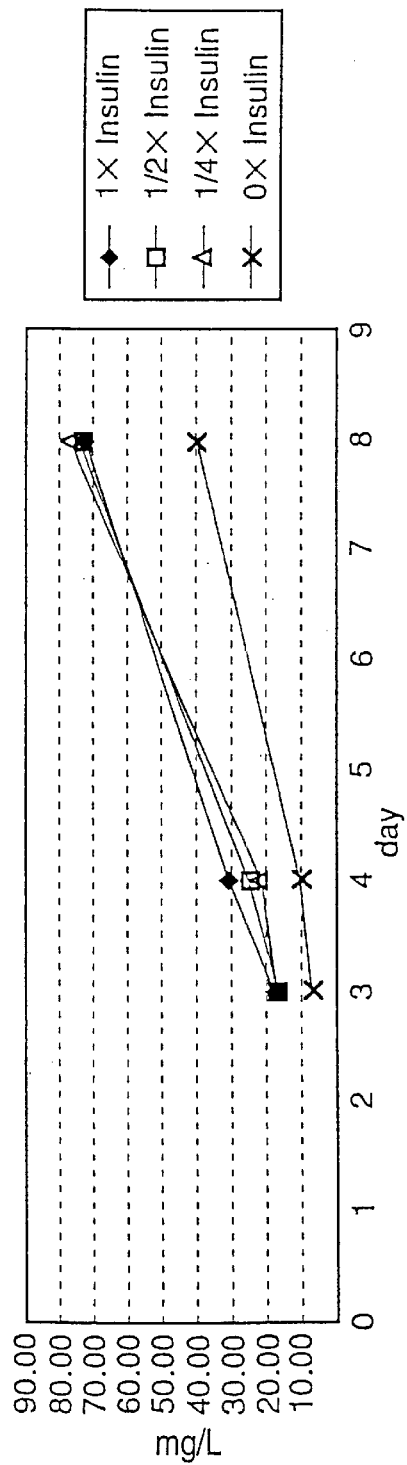
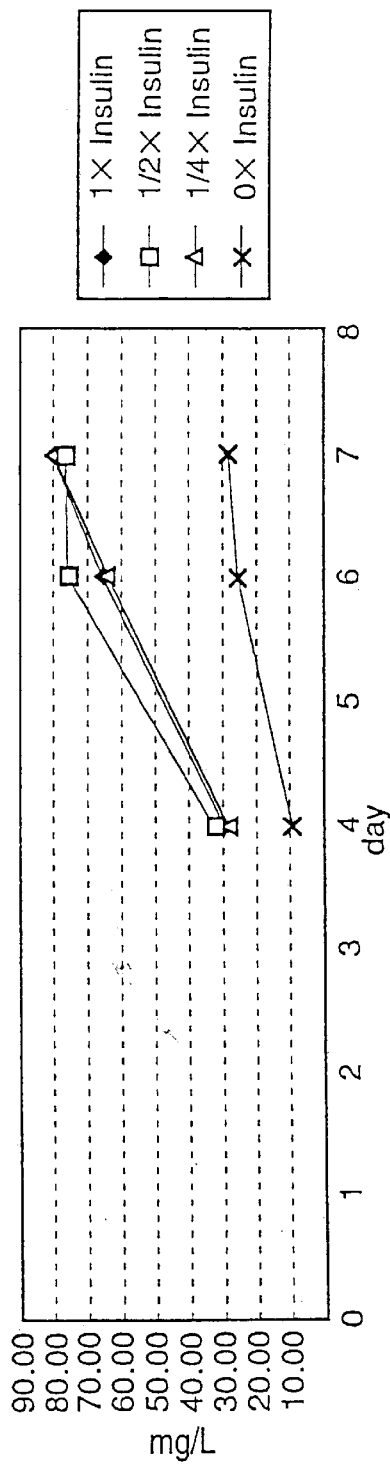

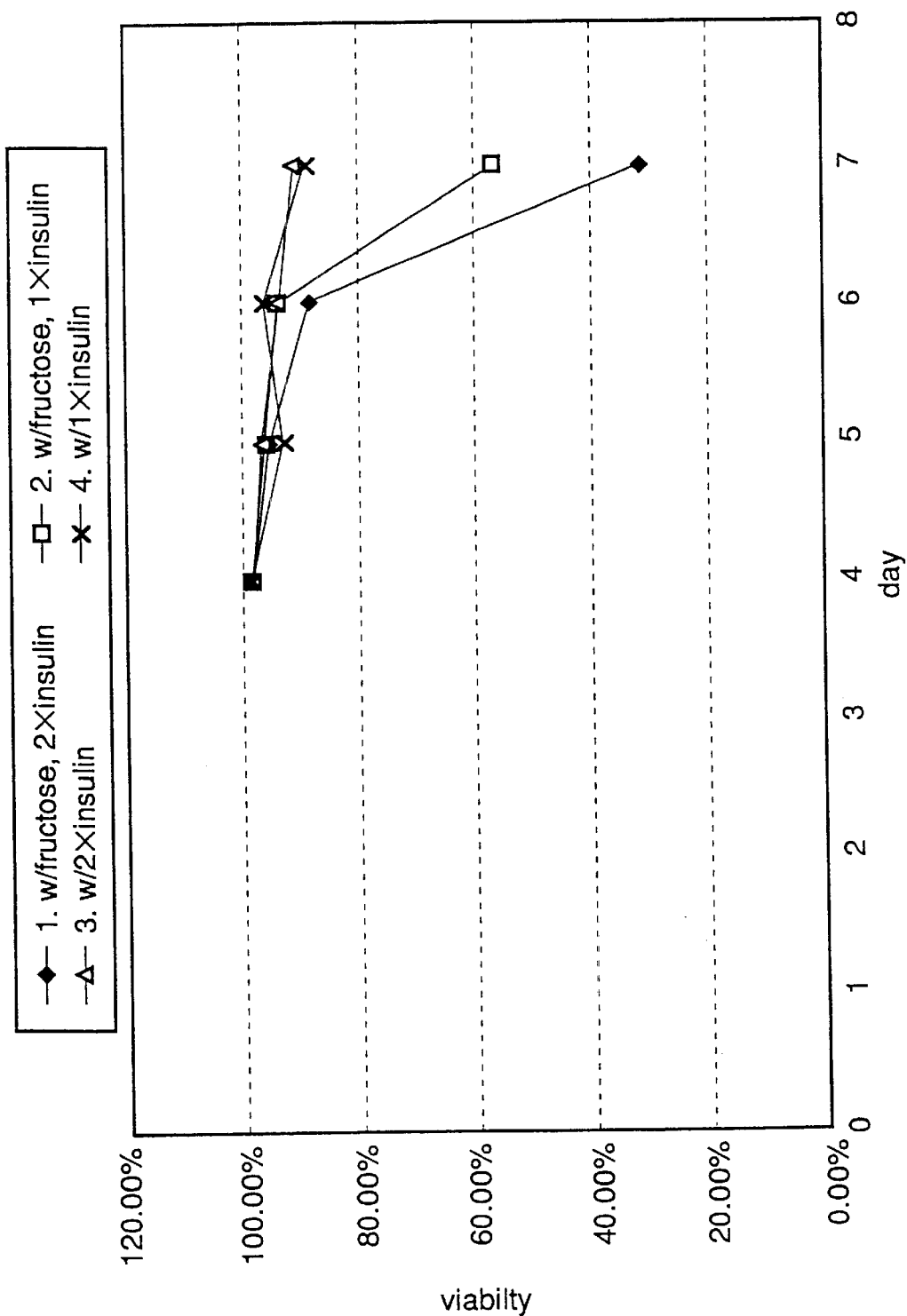

SERUM-FREE MEDIUM FOR CULTURING ANIMAL CELLS

BACKGROUND OF THE INVENTION

The present invention relates to a serum-free medium for culturing animal cells, a method for culturing animal cells using the medium, and a method for producing a substance by culturing animal cells in the medium.

Methods for artificial production of various proteins and peptides using recombinant DNA techniques have been developed. Also, methods for creating and culturing transformed cells for use in such methods have been studied. Among these transformed cells, mammal-derived cells are used as host cells for recombinant production of human-derived proteins, etc. to be used in pharmaceuticals. Some of mammal-derived cells are used as host cells. One of the most commonly used mammal-derived cells is Chinese hamster ovary (CHO) cells. As to various selection markers, methods for selecting recombinant cell clones using the markers and host cells which are necessary for application of recombinant DNA techniques, genetic deficiencies against which various selection markers function effectively and a large number of sub-cell lines exhibiting auxotrophy associated with such genetic deficiencies have been established. Conventionally, a medium containing serum or protein components separated from serum has been commonly used for culturing mammal-derived cells. Recently, however, a serum-free medium has been positively developed in order to eliminate contaminants in serum such as viruses or pathogenic prions which must not remain in final products, e.g. recombinant proteins.

A possibility of causing similar contamination has been suggested in the use of proteins separated from serum, such as serum albumin, transferrin, fetuin, various peptide hormones and growth factor proteins, as well as proteins or peptides separated from animals such as blood-containing tissues like beef hydrolysate. Thus, development of a serum-free medium which does not contain even such proteins or peptides has been pursued. Specifically, various peptide hormones and growth factor proteins added to a medium have been replaced with highly purified, corresponding recombinant products as much as possible. In addition, various attempts have been made to replace those proteins or peptides separated from animals with those proteins, peptides or lipids separated from non-animal cells.

A serum-free medium now under development is a basal medium supplemented with various peptide hormones and growth factor proteins for the induction or promotion of cell growth. The basal medium contains appropriate quantities of the substances composing the transformed cells to be cultured (specifically, raw materials such as amino acids, precursors of nucleic acids or nucleosides, aliphatic acids, etc. to be used in the biosynthesis of various proteins, peptides, lipids, nucleic acids, etc. in cultured cells), as well as those constituents of cytoplasm and the like which are taken up from the outside of the cells and used as cell constituents/components per se at the time of cell growth and division (e.g., metal elements, phosphates, chloride ions, and vitamins to be used in coenzymes for enzymes).

In addition to the above-mentioned components essential for the induction or promotion of cell growth per se, addition of supplementary components to maintain the cultivation rate at a high level is under review. Further, addition of supplementary components to promote the production of a gene product of interest, notably recombinant protein or the like, in the transformed cells in culture or to maintain such production at a high level is under review. It is expected to propose a serum-free medium having a cultivation ability comparable to that of the conventional serum-containing medium through selection of the above-mentioned supplementary components to be added to the medium and selection of the optimum amounts of addition of such components. In particular, a new proposal of a serum-free medium is awaited which can achieve an ability comparable to that of the conventional serum-containing medium in culturing animal-derived cells, especially CHO cells, commonly used in the recombinant production of human-derived proteins for use in pharmaceuticals. Furthermore, proposal of a method for culturing animal cells, especially CHO cells, using such a new serum-free medium, as well as a method for performing recombinant production of a human-derived protein of interest at a high efficient by such culturing is also desired.

The present invention has been made to solve the above problems. It is an object of the invention to provide a serum-free medium for culturing animal cells.

It is another object of the invention to provide a method for culturing animal cells in the serum-free medium.

It is still another object of the invention to provide a method which, through the cultivation of animal cells in the serum-free medium, yields a substance that is produced by and secreted out of the animal cells.

SUMMARY OF THE INVENTION

Toward the solution of the above-mentioned problems, the present inventors have made extensive and intensive researches. As a result, it was found that growth of animal cells, in particular CHO cells, can be achieved in a serum-free medium which is obtained by adding various peptide hormones and growth factor proteins for induction or promotion of cell growth to a basal medium containing appropriate quantities of various components taken up by the cells from the outside and used as cell constituents/components per se. Subsequently, the inventors have optimized the composition of the basal medium in order to maintain the growth rate at a high level. However, the growth rate of animal cells, in particular CHO cells, was still significantly inferior to the growth rate achieved in the serum-free medium described above supplemented with serum or serum-derived proteins, proteolysates, peptides, etc. The present inventors have further found out that a cultivation ability comparable to the growth rate achieved in serum-containing media can be achieved in a serum-free medium by replacing the components of serum-containing media separated from animals (such as serum or serum-derived proteins, proteolysates, peptides) with a specific combination of components derived from plants and components derived from microorganisms which do not exhibit pathogenicity against human or mammals and by selecting optimum amounts of addition of such components. Based on these findings, the present invention has been achieved.

The present invention provides a serum-free medium for culturing animal cells, containing soybean protein hydrolysate and yeast extract. The serum-free medium of the invention may further comprise wheat protein hydrolysate. By using the serum-free medium of the invention, animal cells can be cultured without addition of components separated from animals, such as serum or serum-derived proteins, proteolysates, peptides. The soybean protein hydrolysate may be added at 1–5 g per liter of the medium. The yeast extract may be added at 1–5 g per liter of the medium. In such a case, wheat protein hydrolysate may be added at a rate of 0.5–3 g per liter of the medium. The ratio by weight of the amount of addition of soybean protein hydrolysate to the amount of addition of yeast extract may be in the range from 80:20 to 60:40. In such a case, the amount of addition of wheat protein hydrolysate may come within the range from 5 to 60% of the total weight of the soybean protein hydrolysate and the yeast extract added. By using the serum-free medium of the invention, it is possible to culture animal cells, preferably mammalian cells, more preferably Chinese hamster ovary (CHO) cells. The animal cells may be transformed cells into which a foreign gene has been transferred.

The present invention also provide a method for culturing animal cells, comprising a step of culturing animal cells in a serum-free medium containing soybean protein hydrolysate and yeast extract. The animal cells are preferably mammalian cells, more preferably CHO cells. The animal cells may be transformed cells into which a foreign gene has been transferred.

Further, the present invention provides a method for producing a substance, comprising a step of culturing animal cells in a serum-free medium containing soybean protein hydrolysate and yeast extract to thereby allow the animal cells to produce the substance and secrete it out of the cells and a step of isolating the substance from the serum-free medium. The substance may be a protein or peptide. The animal cells may be transformed cells into which a foreign gene has been transferred. The substance produced by and secreted out of the animal cells may be a gene product from the transferred gene, e.g., a recombinant protein or peptide. In this method, the animal cells are preferably mammalian cells, more preferably CHO cells.

BRIEF DESCRIPTION OF THE DRAWINGS

FIGS. 8a and 8b are graphs showing the effect of the amount of insulin added on the yield of a recombinant protein by transformed CHO cells when subcultured in the presence of wheat protein hydrolysate in the medium in addition to soybean protein hydrolysate and yeast extract.

FIG. 9 is a graph showing the effect of the amount of addition of insulin on the viability of transformed CHO cells when subcultured in the presence of wheat protein hydrolysate in the medium containing fructose or glucose in addition to soybean protein hydrolysate and yeast extract.

DESCRIPTION OF PREFERRED EMBODIMENTS

Figure 1:
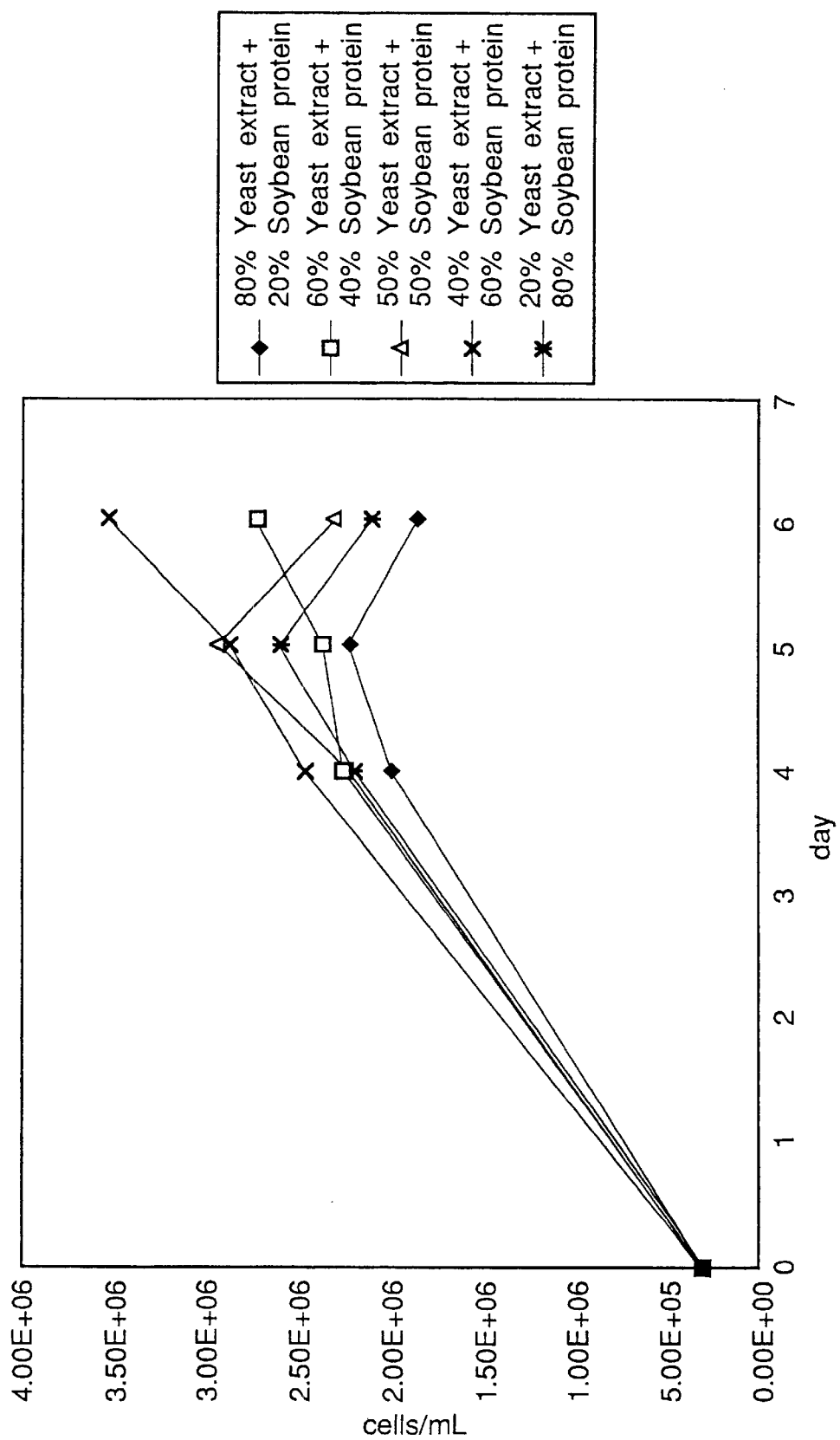
FIG. 1 is a graph showing the effect of the amounts of addition of soybean protein hydrolysate and yeast extract on the growth rate of transformed CHO cells.

Hereinbelow, one embodiment of the invention will be described.

The serum-free medium of the invention may be used for culturing animal cells, preferably mammalian cells, and more preferably CHO cells. The term "serum-free medium" as used herein means a medium which does not contain serum or any serum components such as proteins separated from serum. Furthermore, the serum-free medium of the invention does not contain any components separated from animals, to say nothing of the above-mentioned serum or serum components such as proteins separated from serum.

Animal cells which can be cultured in the serum-free medium of the invention included: mammal cells such as CHO cells, HeLa cells, baby hamster kidney (BHK) cells, rodent myeloma cells; insect cells such as Drosophila cell lines; and transformed cells obtained by transferring a foreign gene in to these cells.

The serum-free medium of the invention contains, as its basal medium components, specific amounts of various nutrient components which are selected from inorganic substances, synthetic substances and plant-derived components and which are taken up from the outside by the animal cells to be cultured and used as cell constituents/components per se, and specific amounts of synthetic or recombinant peptide hormones or cell growth factors which directly act on the animal cells to induce or promote their cell growth. In addition to these basal medium components, the medium of the invention contains soybean protein hydrolysate and yeast extract as supplementary components. More preferably, wheat protein hydrolysate is also added to the medium of the invention.

The serum-free medium of the invention does not contain any components separated from animals. The components separated from animals mean not only serum but also proteins separated from serum (e.g., serum albumin, transferrin, fetuin, various peptide hormones, growth factor proteins), proteins and peptides separated from animals such as blood-containing tissues (e.g., beef hydrolysate), and organic components separated from animal sources (e.g., lipids and carbohydrates) and so on. Here, the animals include not only mammals but also insects, birds, reptiles, etc. which are believed to be involved in the carrying of such pathogens as virus infectious to mammals.

The various nutrient components to be added to the serum-free medium of the invention as basal medium components include the components mentioned in Table 1 below. These components are taken up from the outside by the animal cells (preferably mammal cells, more preferably CHO cells) to be cultured and used as cell constituents/components per se, and they are selected from inorganic substances, synthetic substances and plant-derived components. Specifically, the basal medium components include various amino acids, nuclear acids or precursors thereof, essential metals and inorganic ions, lipids, vitamins, coenzymes and cofactors, organic substances to be used as energy sources, carbon sources and nitrogen sources. These components are used during the process of biosynthesis of various biological substances constituting the animal cells. The basal medium components further include various peptide hormones and growth factor proteins that are not directly separated from animals, i.e., those which are produced with recombinant techniques, synthesized artificially or separated from plants. Besides those components, various buffer components for maintaining the pH at a desired level and inorganic osmotic pressure adjustors for controlling the osmotic pressure at a desired level are also added to the medium of the invention.

Specific examples of the amounts of addition of various nutrient components as the basal medium components are shown in Table 1, these amounts being particularly preferred for culturing CHO cells.

TABLE 1

Basal Medium Composition: A Representative Example

| Component | Amount of Addition (mg/L) |
|---|---|
| Sodium Chloride | An amount necessary to give a specified osmotic pressure |
| Potassium Chloride | 313.8 |
| Glucose (Dextrose) anhyd. | 8000 |
| L-Alanine | 16.955 |
| L-Arginine HCl | 168.845 |
| L-Asparagine H$_2$O | 32.5~65.0 |
| L-Asparatic Acid | 21.655 |
| L-Cysteine HCl H$_2$O | 128~256 |
| L-Glutamic Acid | 44.855 |
| L-Glutamine | 1169.2 |
| Glycine | 28.755 |
| L-Histidine HCl H$_2$O | 31.425 |
| L-Isoleucine | 27.97 |
| L-Leucine | 32.56 |
| L-Lysine HCl | 54.505 |
| L-Methionine | 9.74~19.48 |
| L-Phenylalanine | 18.48 |
| L-Proline | 37.265~74.53 |
| L-Serine | 17.755~35.51 |
| L-Threonine | 29.955 |
| L-Tryptophan | 6.02~12.04 |
| L-Tyrosine 2Na 2H$_2$O | 29.865 |
| L-Valine | 28.855 |
| Ascorbic Acid | 25 |
| Folic Acid | 1.16 |
| Inositol | 10.01 |
| Nicotinic Acid Amide | 0.5185 |

TABLE 1-continued

Basal Medium Composition: A Representative Example

| Component | Amount of Addition (mg/L) |
|---|---|
| Riboflavin | 0.069 |
| Sodium Selenite | 0.004324 |
| Thiamine HCl | 0.6685 |
| Thioctic Acid, D-L (Liopoic Acid) | 0.203 |
| Cytidine | 0~5 |
| 2' Deoxyadenosine 1H$_2$O | 0~5 |
| 2' Deoxycytidine HCl | 0~5 |
| 2' Deoxyguanosine | 0~5 |
| Guanosine | 0~5 |
| Uridine | 0~5 |
| Adenosine | 0~5 |
| Pyridoxine HCl | 0.031 |
| Putrescine 2HCl | 0.0805 |
| Cupric Sulfate CuSO$_4$ 5H$_2$O | 0.00125 |
| Ferrous Sulfate FeSO$_4$ 7H$_2$O | 0.417 |
| Zinc Sulfate ZnSO$_4$ 7H$_2$O | 0.4315 |
| d-Biotin | 0.05365 |
| Pantothenic Acid Ca salt | 0.619 |
| Vitamin B12 (aka CYANOCOBALAMIN) | 1.36 |
| Pyridoxal HCl | 0.5 |
| Pyruvic Acid, Na salt | 110 |
| NaH$_2$ PO$_4$ H$_2$O | 70 |
| Na$_2$ HPO$_4$ anhyd. | 82.49 |
| Calcium Chloride anhyd. | 116.65 |
| Magnesium Chloride anhyd. | 28.57 |
| Magnesium Sulfate | 50 |
| Ethanolamine HCl | 1.95 |
| KH$_2$ PO$_4$ | 2 |
| Choline Chloride | 7.48 |
| Pluronic F-68 | 1000 |
| EDTA Ferric-Sodium Salt Dihydrate | 25.0 |
| Insulin Human Recombinant | 5 |
| Sodium Bicarbonate | 1608 |

In Table 1 above, an iron-EDTA complex is also used as an iron source in addition to an inorganic iron salt. The amount of addition of this complex represents the final concentration in the medium when the preparation of the medium has been completed. The basal medium composition described above sufficiently contains various nutrient components which are used by the cells in the biosynthesis of necessary substances for constituting the cells, e.g., cell membrane, nuclear membrane, peptides, proteins, various DNAs and RNAs. These nutrient components include essential and non-essential amino acids necessary for CHO cells; monosaccharides to be used as carbon sources or energy sources; various nucleic acids and vitamins; lipids and aliphatic acids necessary for CHO cells; electrolyte ions, metal ions and acids to be contained in the cytoplasm; and various metal elements and co-enzymes to be used by enzyme proteins. The nutrient components described above are taken up and absorbed by the cells from the medium, and used for the maintenance and division of the cells. Further, buffer components to retain the pH of the medium at an appropriate level for the cultivation and osmotic pressure adjusting components to maintain an appropriate osmotic pressure are also contained in proper amounts. In the basal medium described in Table 1, the pH is adjusted in the range from 7.0 to 7.5 and the osmotic pressure in the range from 280 to 320. Most preferably, the amounts of NaHCO$_3$, etc. (buffer components) and the amounts of NaCl, etc. (osmotic pressure adjusting components) in the medium are adjusted so that the pH of the medium comes within the range from 7.2 to 7.4 and the osmotic pressure within the range from 290 to 300.

The composition shown in Table 1 is just one representative composition of the basal medium which may be used in the medium of the invention and one or more of the components listed in Table 1 may be replaced with equivalent components. For example, two substances equivalent with each other, such as amino acids cysteine and cystine, may be interchanged. With respect to metal elements, salts other than those listed in Table 1 may be used as long as they are water-soluble inorganic salts and can be used in a medium for culturing animal cells. Also, a part of glucose which is commonly used as a monosaccharide may be replaced with fructose. Certain vitamins such as vitamin $B_{12}$ consist of several compounds that have similar actions and are interchangeable. A part of such vitamins may be replaced with such equivalent compounds. As to the nutrients required by CHO cells to be cultured or the additional components to be added to detect the presence of a marker gene used in DNA recombination, appropriate amounts may be added as needed by the characteristics of the transformed CHO cells to which those nutrients and components are applied. Further, in order to detect the presence of the marker gene used in DNA recombination, those components which may hinder the detection can be eliminated even if they are listed in Table 1.

As to the various peptide hormones and growth factor proteins which are added to the serum-free medium of the invention so that they act directly on animal cells to thereby induce or promote cell growth, synthetic or recombinantly produced hormones and proteins are used. This means that those which are synthesized or recombinantly produced and sufficiently purified that they are free from unwanted contamination as with virus, mycoplasma, pathogenic prion, etc. should be used. Peptide hormones or cell growth factors which were already reported to act on animal cells directly to thereby induce or promote cell growth have been added to a medium conventionally. They may be used similarly in the present invention. Specific examples of the peptide hormones or cell growth factors which induce or promote cell growth include recombinant insulin, recombinant insulins having a modified amino acid sequence and exhibiting a physiological activity comparable to that of natural insulin, and recombinant insulin-like growth factor. As the recombinant insulins, a recombinant human insulin may be used. For example, a commercial recombinant human insulin such as nucellin (product name) may be used.

Hereinbelow, the effect of soybean protein hydrolysate, yeast extract and wheat protein hydrolysate which characterize the serum-free medium of the invention most will be described. Although these three supplementary components are not essential components for culturing animal cells, they are effective in maintaining at high level the rate of the cell growth induced or promoted by the above-mentioned peptide hormones or cell growth factors, or in further increasing the growth rate. In addition, these three components are effective in promoting the production of a recombinant protein or peptide of interest which is achieved by culturing recombinant animal cells, or in maintaining the production rate at high level.

In other words, cultivation of cells can be achieved with the basal components alone (i.e., the serum-free medium of the invention without soybean protein hydrolysate, yeast extract and wheat protein hydrolysate) though the cultivation rate is low.) The technical significance of the serum-free medium of the invention is that appropriate amounts of soybean protein hydrolysate, yeast extract and wheat protein hydrolysate are added as supplementary components to the basal medium components to thereby achieve a higher cultivation efficiency. In view of the effect of these three components, they are regarded as supplementary components to the basal medium.

Among the three components of the present invention, the component which mainly contributes to maintain the growth rate at high level or further improve the growth rate is soybean protein hydrolysate; and the component which mainly contributes to maintain the production rate of a recombinant protein or peptide of interest at high level or the promote such production is yeast extract. By contrast, wheat protein hydrolysate is effective in reducing the mortality of the recombinant animal cells during production of a recombinant protein or peptide of interest. Thus, wheat protein hydrolysate manifests its effect well when added to the medium together with soybean protein hydrolysate and yeast extract, rather than added to the medium alone.

The soybean protein hydrolysate used in the invention may be a soybean protein hydrolysate obtained from soybean of any quality. Preferably, a commercial soybean protein hydrolysate used for culturing microorganisms, e.g., DMVSE50MK (DMV), DMVSE50MAF (DMV), HyPep 1601 (Quest), Soy Protein Hydrolysate: Hysoy (Quest), or the like is used. Soybean protein hydrolysate may be converted to a soluble polypeptide by partial hydrolysis with various enzymes such as digestive enzymes.

Yeast extract is also available as commercial products for use in culturing microorganisms. Preferably, a commercial yeast extract such as HyYeast 455 (refined yeast extract; Quest), Springer Yeast Extract UF10 (Bio Springer), Fermax 5902AG (Red Star) or the like is used. Yeast extract is a material which is obtained by crushing dry yeast and separating the intracellular soluble fraction by extraction. Yeast extract is available as a material containing various coenzymes and cofactors.

The wheat protein hydrolysate used in the invention may be a wheat protein hydrolysate obtained from wheat of any quality. Preferably, a commercial wheat protein hydrolysate used for culturing microorganisms, e.g., HyPep 4402 (Quest) is used. Wheat protein hydrolysate may be obtained as a soluble polypeptide by partially hydrolyzing protein as in wheat embryos with various digestive enzymes.

Soybean protein hydrolysate, yeast extract and wheat protein hydrolysate are commercially available in various forms, and it is convenient to use such commercial products. It is particularly preferable to use commercial products intended for culturing microorganisms. In the composition of the medium of the invention, the amounts of addition of these components are expressed in dry weight. The amount of addition of soybean protein hydrolysate is selected depending on the animal cell density at the beginning of cultivation. The amount is selected from the range of at least 1 to 6 g/liter; usually from the range of 1 to 5 g/liter; preferably from the range of 2 to 4 g/liter. The amount of addition of yeast extract is selected depending on the rate of rise of the animal cell density as a result of the cultivation. The amount is selected from the range of at least 0.5 to 5 g/liter; usually from the range of 1 to 5 g/liter; preferably from the range of 1 to 3 g/liter. In addition, for the purpose of increasing the yield of a recombinant protein of interest from the cultured cells, it is necessary to promote the cultivation and make the animal cell density higher than a desired value. To this end, it is preferable to make the amount of addition of soybean protein hydrolysate greater than the amount of addition of yeast extract. Therefore, the ratio (by weight) of the amount of addition of soybean protein hydrolysate to the amount of addition of yeast extract is preferably at least 50:50, more preferably at least 60:40. On the other hand, if the amount of addition of yeast extract is unduly small, the effectiveness in promoting the production of a recombinant protein in cultured cells is insufficient. Considering this point, the ratio (by weight) of the amount of addition of soybean protein hydrolysate to the amount of addition of yeast extract is preferably not more than 90:10, more preferably 80:20 or less. Considering these two conditions together, the ratio (by weight) of the amount of addition of soybean protein hydrolysate to the amount of addition of yeast extract is preferably in the range of 50:50 to 90:10, more preferably in the range of 60:40 to 80:20.

In the medium of the invention, wheat protein hydrolysate is effective in improving the cultivation rate and reducing the cell death resulting from the production of a recombinant protein or peptide by the cultured cells. Thus, the amount of addition of wheat protein hydrolysate is selected considering the above-mentioned amounts of addition of soybean protein hydrolysate and yeast extract.

In particular, it is preferable to select this amount depending on the amount of addition of yeast extract. When the amount of addition of yeast extract is in the range from 1 to 5 g/liter, the amount of addition of wheat protein hydrolysate is preferably in the range from 0.5 to 3 g/liter. In particular, when the amount of addition of yeast extract is in the range from 1 to 3 g/liter, the amount of addition of wheat protein hydrolysate is more preferably in the range from 0.5 to 2 g/liter, particularly preferably around 1 g/liter. Alternatively, under the condition that the ratio (by weight) of the amount of addition of soybean protein hydrolysate to the amount of addition of yeast extract is selected from the range of 60:40 to 80:20, the amount of addition of wheat protein hydrolysate is selected preferably from the range of 5 to 60%, more preferably from the range of 10 to 40%, of the total weight of the soybean protein hydrolysate and the yeast extract added. Further, under the condition that the amount of addition of soybean protein is selected from the range of 2 to 4 g/liter and the amount of addition of yeast extract is selected from the range of 1 to 3 g/liter, it is more preferable to select the amount of addition of wheat protein hydrolysate from the range of 10 to 40% of the total weight of the soybean protein hydrolysate and the yeast extract added.

In the medium of the invention, the promotion and maintenance of cultivation rate and the promotion of the production of a recombinant protein or peptide by the cultured cells are achieved by adding soybean protein hydrolysate and yeast extract in the preferable amounts stated above. The effects of these two components can be further increased by also adding wheat protein hydrolysate in the preferable amount stated above. A particular advantage to the promotion and maintenance of cultivation rate results from the addition of wheat protein hydrolysate as well as the above two components since this is effective in widening the allowable range of the amounts of addition of peptide hormones and cell growth factors for inducing and promoting the cell growth. Specifically, even if the amounts of addition of peptide hormones and cell growth factors are reduced, a sufficient cultivation rate can be achieved and yet the yield of the recombinant protein or peptide produced by the cultured cells can be stabilized at high level. For example, the amount of addition of recombinant insulin as the above-mentioned peptide hormone/cell growth factor to induce and promote the cell growth is usually 5 mg/liter; this amount can be reduced to 1 mg/liter while maintaining a sufficient cultivation rate, if wheat protein hydrolysate is added to the medium in addition to soybean protein hydrolysate and yeast extract.

The serum-free medium of the invention can be prepared by adding each of the above-described components to an appropriate amount of water, dissolving or suspending them, homogenizing the components in the resultant medium, and finally adding a small amount of water to the medium to make a specified volume. Except yeast extract, the components to be added to the serum-free medium of the invention are chiefly selected from inorganic substances, synthetic substances, plant-derived components, plant-derived protein hydrolysates, and recombinant proteins or peptides produced with recombinant DNA techniques. A part of the amino acids to be added to the medium may be such amino acids that are synthesized from starting materials by an enzyme reaction using a microorganism or an enzyme it produces and then purified.

Animal cells, preferably mammal cells, more preferably CHO cells can be cultured using the serum-free medium of the invention containing soybean protein hydrolysate, yeast extract and, optionally, wheat protein hydrolysate. Specific examples of the animal cells are as described previously. In a method of culturing CHO cells, for example, cells are seeded in the medium at an initial density of $1-5\times10^5$ cells/ml, preferably $2-4\times10^5$ cells/ml and cultured at 37° C. under 5% $CO_2$. The cultivation method using the serum-free medium of the invention is applicable to transformed CHO cells for use in the production of various recombinant proteins or peptides. Specific examples of the recombinant protein or peptide produced by culturing such transformed CHO cells include human t-PA, human immune interferon γ, human interferon β, granulocyte colony stimulating factor (G-CSF), granulocyte macrophage colony stimulating factor (GM-CSF), erythropoietin, interleukins such as IL-1, IL-6, urokinase, albumin, blood coagulation factor VIII, and recombinant antibodies such as humanized PM-1 antibody. These substances are secreted from the cultured cells and accumulated in the medium. After the cultivation, the cells are separated from the medium, and then the recombinant protein of interest is isolated and purified by conventional methods.

Hereinbelow, the serum-free medium of the invention, a method for culturing CHO cells using the medium, and a method for producing a recombinant protein by culturing transformed CHO cells are described with reference to specific examples. In the following examples, a humanized anti-human IL-6 receptor antibody-producing transformed CHO cell clone is used as the transformed CHO cell, and a system to produce the humanized anti-human IL-6 receptor antibody as the recombinant protein is described. It should, however, be noted that the serum-free medium of the invention can be used for culturing not only those transformed CHO cells which are obtained by using DHFR gene-deficient CHO cell clone as a host cell and DHFR gene as a selection marker, but also other transformed CHO cells which are obtained by using other selection marker such as glutamine synthetase gene. In the latter case, the serum-free medium of the invention can also achieve an extremely efficient cell growth and stabilization thereof.

PREPARATION EXAMPLE

Preparation of a Humanized Anti-Human IL-6 Receptor Antibody-Producing Transformed CHO Cell Clone A humanized anti-human IL-6 receptor antibody-producing transformed CHO cell clone was obtained by transferring into a host cell a DHFR gene-deficient CHO cell clone [a dihydrofolate reductase-deficient clone (DXB11 cells) separated from KI clone after treatment with $^3$H-deoxyuridine; described in L. H. Grof, L. A. Chasin, Mol. Cell Biol. 2, 93 (1982)] a gene coding for a recombinant protein, a humanized anti-human IL-6 receptor antibody (humanized PM-1 antibody) [Koh Sato et al., Cancer Research, 53, 851–856 (1993)] based on the method described in Reference Example 2 in Japanese Unexamined Patent Publication No. 8-99902. In this transformed CHO cell clone, the gene coding for the humanized PM-1 antibody is incorporated downstream of the promoter of human elongation factor I α described in Example 10 of WO92/19759. Thus, the transcription and translation of the gene into the humanized PM-1 antibody of interest are performed under the control of the above-mentioned promoter.

In brief, an expression vector was introduced into DXB11 cells by el. Thereafter, colonies surviving in a selection medium (containing bovine serum but not containing nucleotides) were selected.

EXAMPLE 1

Addition of Soybean Protein Hydrolysate and Yeast Extract

It was demonstrated that by adding soybean protein hydrolysate and yeast extract to a serum-free medium, the medium can achieve a remarkable improvement in the cultivation rate of transformed CHO cells and in the yield of the recombinant protein produced by the cultured cells. The correlation between the improvement and the amounts of addition of soybean protein hydrolysate and yeast extract was also examined. As soybean protein hydrolysate, a commercial product HySoy (Quest) was used, and as yeast extract a commercial product UF10 (Bio Springer) was used.

The soybean protein hydrolysate and the yeast extract were added to the basal medium composition shown in Table 2 below to prepare a serum-free medium. The total amounts of addition of the soybean protein hydrolysate and the yeast extract was 5 g/liter. While varying the ratio (by weight) of the amount of addition of soybean protein hydrolysate to the amount of addition of yeast extract, cell counts on day 4 of the cultivation and thereafter, cell viabilities from day 4 to day 7, and the total amounts of the recombinant protein accumulated in the medium up to day 7 were compared.

TABLE 2

Basal Medium Components B

| Component | Amount of Addition (mg/L) |
|---|---|
| Sodium Chloride | 1025 |
| Potassium Chloride | 313.8 |
| Glucose (Dextrose) anhyd. | 8000 |
| L-Alanine | 16.955 |
| L-Arginine HCl | 168.845 |
| L-Asparagine H$_2$O | 32.5 |
| L-Asparatic Acid | 21.655 |
| L-Cysteine HCl H$_2$O | 67.565 |
| L-Cystine 2Na Salt | 14.195 |
| L-Glutamic Acid | 44.855 |
| L-Glutamine | 1169.2 |
| Glycine | 28.755 |
| L-Histidine HCl H$_2$O | 31.425 |
| L-Isoleucine | 27.97 |
| L-Leucine | 32.56 |
| L-Lysine HCl | 54.505 |
| L-Methionine | 9.74 |
| L-Phenylalanine | 18.48 |
| L-Proline | 37.265 |
| L-Serine | 17.755 |
| L-Threonine | 29.955 |
| L-Tryptophan | 6.02 |
| L-Tyrosine 2Na 2H$_2$O | 29.865 |

TABLE 2-continued

Basal Medium Components B

| Component | Amount of Addition (mg/L) |
|---|---|
| L-Valine | 28.855 |
| Ascorbic Acid | 25 |
| Folic Acid | 1.16 |
| Inositol | 10.01 |
| Nicotinic Acid Amide | 0.5185 |
| Riboflavin | 0.069 |
| Sodium Selenite | 0.004324 |
| Thiamine HCl | 0.6685 |
| Thioctic Acid, D-L (Liopoic Acid) | 0.203 |
| Cytidine | 5 |
| 2' Deoxyadenosine 1H$_2$O | 5 |
| 2' Deoxycytidine HCl | 5 |
| 2' Deoxyguanosine | 5 |
| Guanosine | 5 |
| Uridine | 5 |
| Adenosine | 5 |
| Pyridoxine HCl | 0.031 |
| Putrescine 2HCl | 0.0805 |
| Cupric Sulfate CuSO$_4$ 5H$_2$O | 0.00125 |
| Ferrous Sulfate FeSO$_4$ 7H$_2$O | 0.417 |
| Zinc Sulfate ZnSO$_4$ 7H$_2$O | 0.4315 |
| d-Biotin | 0.05365 |
| Pantothenic Acid Ca salt | 0.619 |
| Vitamin B12 (aka CYANOCOBALAMIN) | 1.36 |
| Pyridoxal HCl | 0.5 |
| Pyruvic Acid, Na salt | 110 |
| NaH$_2$ PO$_4$ H$_2$O | 70 |
| Na$_2$ HPO$_4$ anhyd. | 82.49 |
| Calcium Chloride anhyd. | 116.65 |
| Magnesium Chloride anhyd. | 28.57 |
| Magnesium Sulfate | 50 |
| Ethanolamine HCl | 1.95 |
| KH$_2$ PO$_4$ | 2 |
| Choline Chloride | 7.48 |
| Pluronic F-68 | 1000 |
| EDTA Ferric-Sodium Salt Dihydrate | 1 |
| Insulin Human Recombinant | 5 |
| Sodium Bicarbonate | 1608 |

In Table 2 above, an iron-EDTA complex is also used as an iron source in addition to an inorganic iron salt. The amount of addition of this complex represents the final concentration in the medium when the preparation of the medium has been completed.

The culture conditions were as follows. Thirty milliliters of the medium was placed in a 125 ml flask. Cells were seeded at a density of 3.0×10$^5$ cells/ml and cultured under agitation at 160 rpm, at 37° C., under 5% CO$_2$. The results, i.e., cell count on day 4 of the cultivation and thereafter, cell viability from day 4 to day 7, and the total amount of the recombinant protein accumulated in the medium up to day 7 are shown in FIGS. 1, 2 and 3, respectively.

Figure 2:
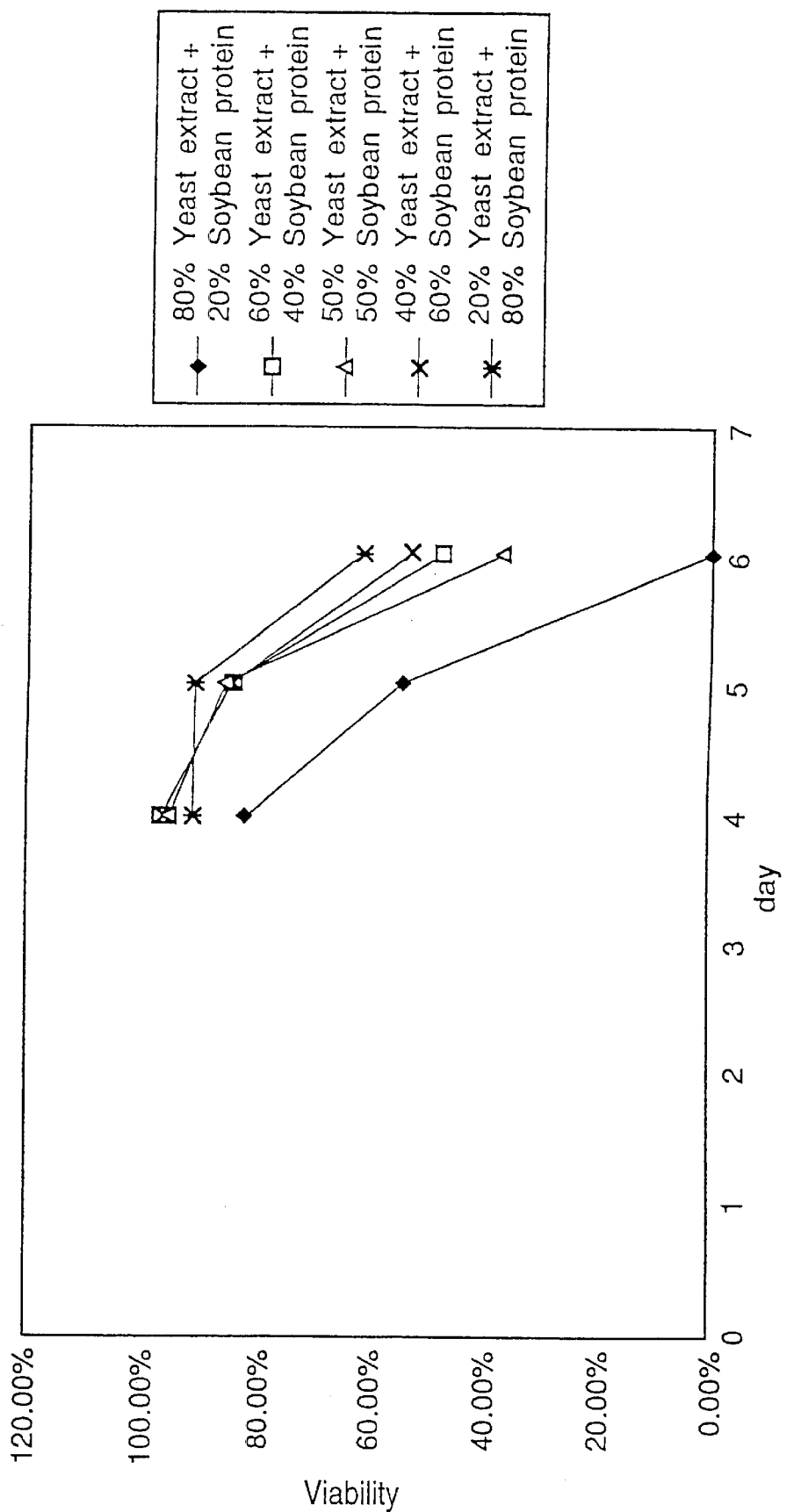
FIG. 2 is a graph showing the effect of the amounts of addition of soybean protein hydrolysate and yeast extract on the viability of transformed CHO cells.
Figure 3:
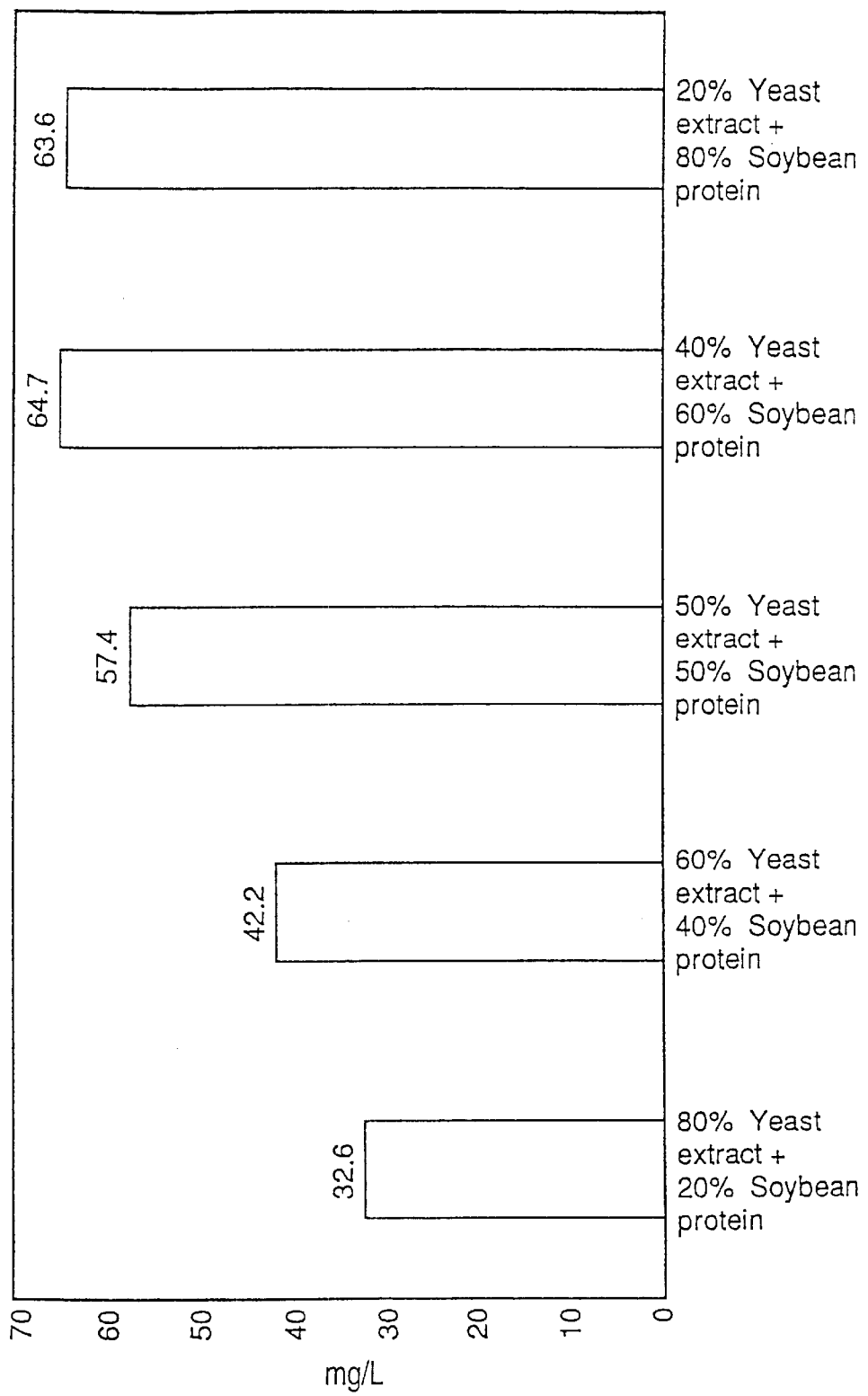
FIG. 3 is a graph showing the effect of the amounts of addition of soybean protein hydrolysate and yeast extract on the yield of a recombinant protein by transformed CHO cells.

From the results shown in FIG. 2, it is understood that the cell viability on day 6 of the cultivation exceeds 50% when the ratio (by weight) of the amount of addition of soybean protein hydrolysate to the amount of addition of yeast extract is 60:40 or 80:20. From the results shown in FIG. 3, it is understood that the total yield of the recombinant protein becomes high when the above ratio is greater than 50:50. However, when the above ratio exceeds 80:20, it is indicated that the total yield tends to decrease.

EXAMPLE 2

Addition of Wheat Protein Hydrolysate

It was demonstrated that by adding to a serum-free medium wheat protein hydrolysate, as well as soybean protein hydrolysate and yeast extract, the medium can achieve not only a remarkable improvement in the cultivation rate of transformed CHO cells and in the yield of the recombinant protein produced by the cultured cells, but also a considerable inhibition of the decrease in cell viability resulting from the production of the recombinant protein in the cultured cells. Also, the amount of addition of wheat protein hydrolysate suitable for inhibiting the decrease in cell viability, and the optimum ranges of the amounts of soybean protein hydrolysate and yeast extract to be added simultaneously and the ratio thereof were examined. As wheat protein hydrolysate, a commercial product HyPep 4402 (Quest) was used.

Soybean protein hydrolysate and yeast extract were added to the basal medium B (for its composition, see Table 2) to prepare a serum-free medium. The total amount of the soybean protein hydrolysate and the yeast extract added was 5 g/liter. Based on the results of Example 1 above, the ratio (by weight) of the amount of addition of soybean protein hydrolysate to the amount of addition of yeast extract was selected at 60:40. To this composition, wheat protein hydrolysate was further added. Using the resultant medium, cell count on day 4 of the cultivation and thereafter, cell viability from day 4 to day 7, and the total amount of the recombinant protein accumulated in the medium up to day 7 were compared.

Figure 5:
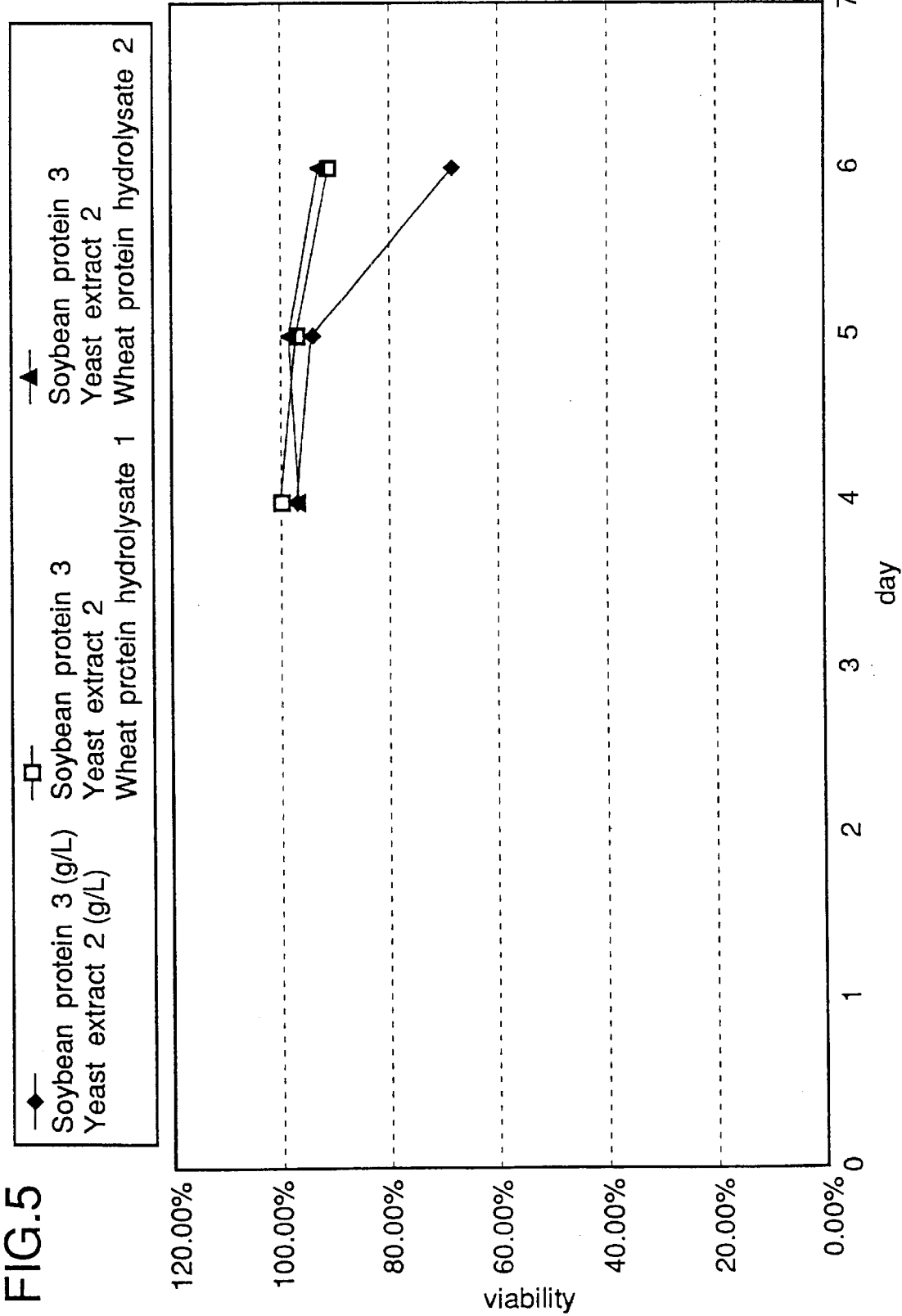
FIG. 5 is a graph showing the effect of addition of wheat protein hydrolysate as well as soybean protein hydrolysate and yeast extract on the viability of transformed CHO cells.
Figure 6:
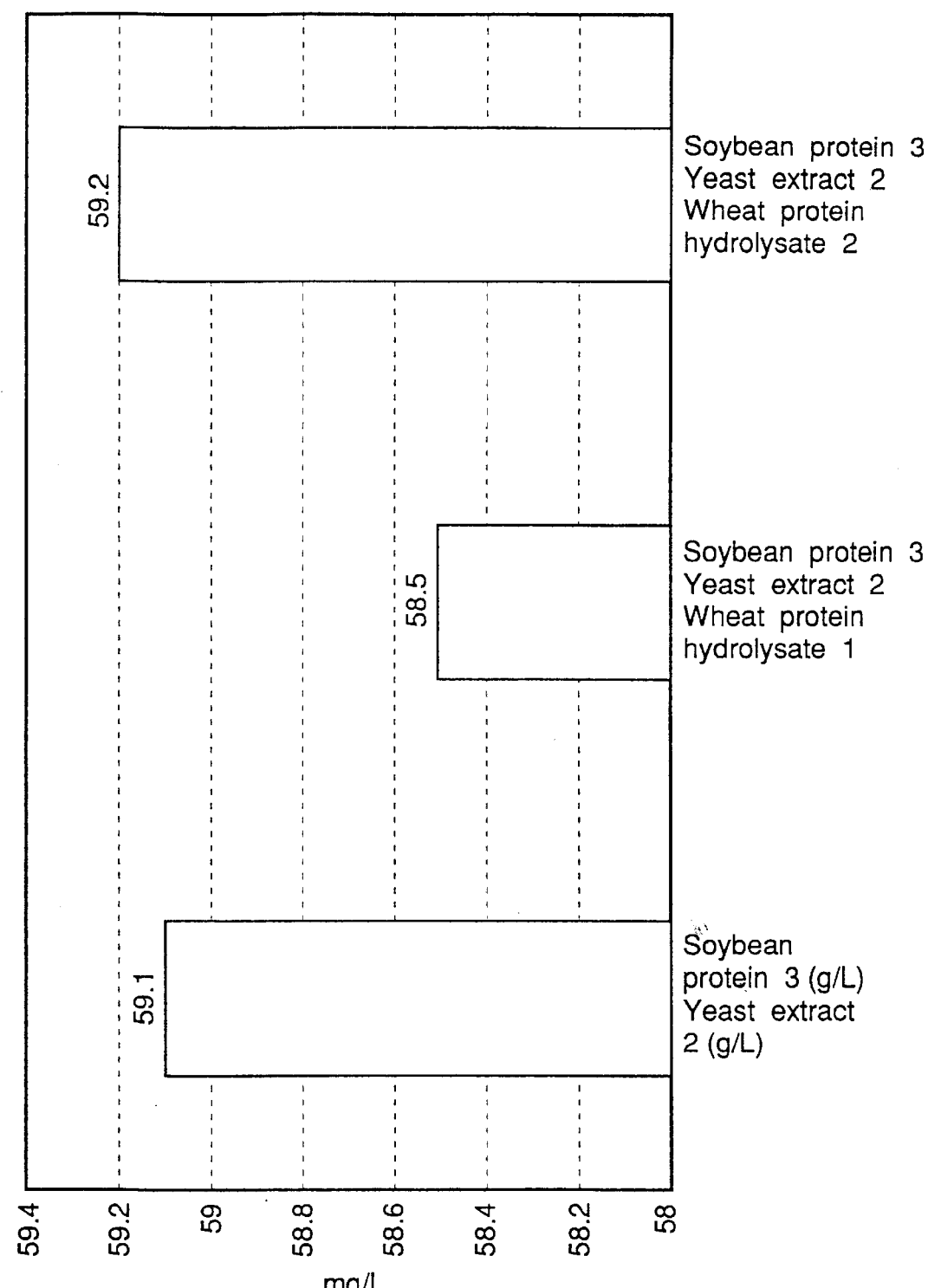
FIG. 6 is a graph showing the effect of addition of wheat protein hydrolysate as well as soybean protein hydrolysate and yeast extract on the yield of a recombinant protein by transformed CHO cells.

Cultivation conditions were as follows. Thirty milliliters of the medium was placed in a 125-ml flask. Cells were seeded at a density of $3.0 \times 10^5$ cells/ml and cultured under agitation at 160 rpm, at 37° C., under 5% $CO_2$. The results, i.e., cell count on day 4 of the cultivation and thereafter, cell viability from day 4 to day 7, and the total amount of the recombinant protein accumulated in the medium up to day 7 are shown in FIGS. 4, 5 and 6, respectively.

Figure 4:
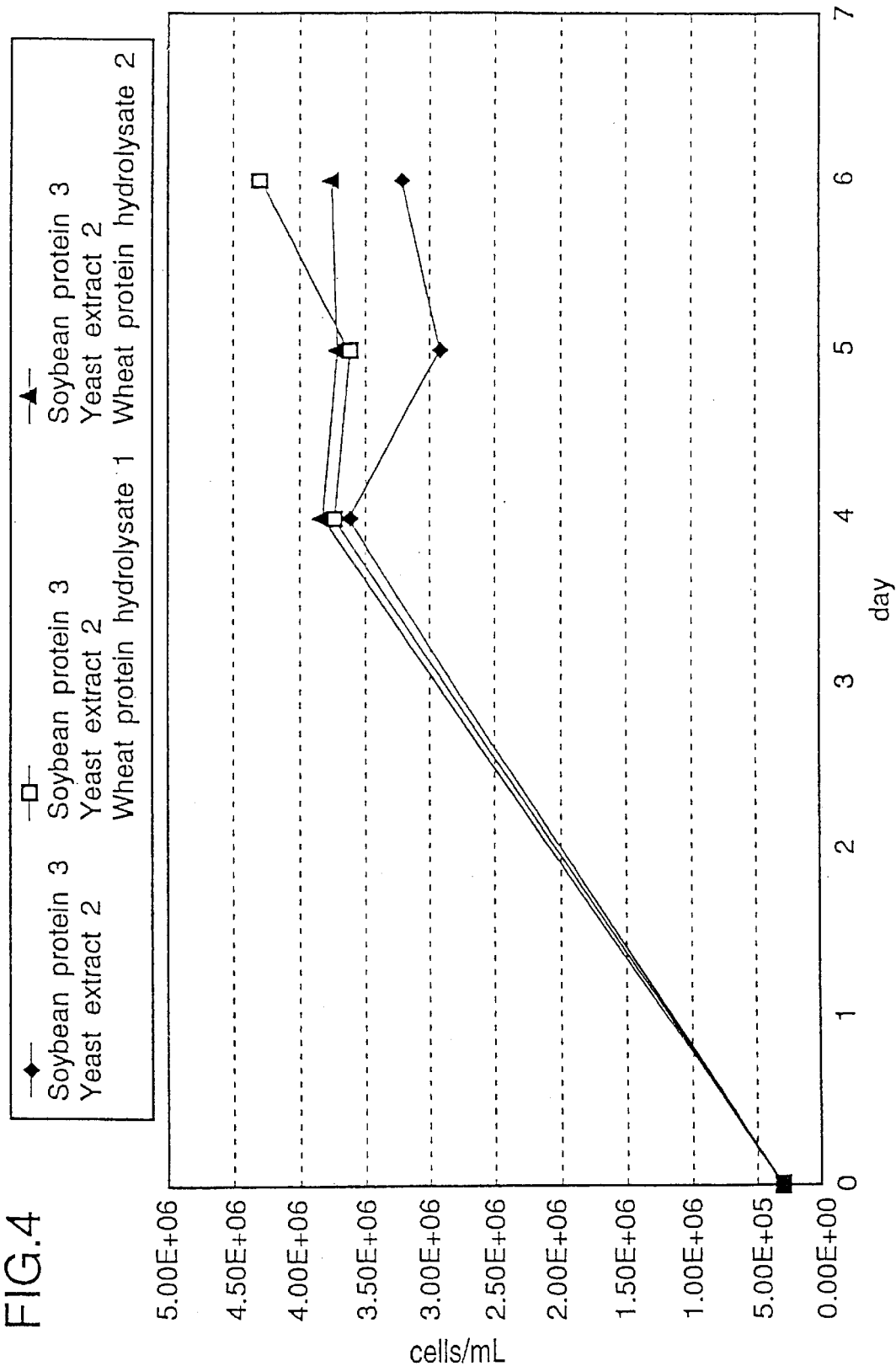
FIG. 4 is a graph showing the effect of addition of wheat protein hydrolysate as well as soybean protein hydrolysate and yeast extract on the growth rate of transformed CHO cells.

As shown in FIG. 4, only a little difference attributable to the presence or absence of wheat protein hydrolysate was observed in the cell count on day 4 of the cultivation. Thereafter, the cell count was maintained or increased when wheat protein hydrolysate was added, but the cell count showed some decrease when wheat protein hydrolysate was not added. As shown in FIG. 5, the viability of the cultured cells did not change on day 4 of the cultivation and thereafter when wheat protein hydrolysate was added; however, the viability showed a significant decrease when wheat protein hydrolysate was not added. In these cases, no difference attributable to the presence or absence of wheat protein hydrolysate or the amount of its addition was observed in the total yield of the recombinant protein accumulated in the medium up to day 7.

From the above results, it was found that by adding soybean protein hydrolysate and yeast extract to the medium in a total amount of 5 g/liter, adjusting the ratio (by weight) of the soybean protein hydrolysate to the yeast extract to 60:40, and adding wheat protein hydrolysate to the medium in an amount up to 2 g/liter, it is possible to remarkably inhibit the decrease in cell viability while maintaining the yield of the recombinant protein. When the amount of addition of wheat protein hydrolysate was further increased, no more increase in cell count was observed. It was particularly found that when wheat protein hydrolysate was added at a dose of 0.5–3 g/liter, usually at a dose of 1–2 g/liter, the above-mentioned improvement could be achieved most effectively. Generally speaking, it was found more preferable to select the amount of addition of wheat protein hydrolysate from the range of 10 to 40% of the total weight of the soybean protein hydrolysate and yeast extract added simultaneously.

As shown in the above example, it was found that a sufficient effect can be achieved by adding wheat protein hydrolysate only at around 1 g/liter when the total weight of soybean protein hydrolysate and yeast extract added is about 5 g per liter of the medium.

EXAMPLE 3

Allowable Range of the Amount of Addition of a Recombinant Insulin When Soybean Protein Hydrolysate, Yeast Extract and Wheat Protein Hydrolysate Are Added It was found possible to maintain or increase the number of cultured cells and to inhibit the decrease in cell viability by adding wheat protein hydrolysate, as well as soybean protein hydrolysate and yeast extract to a serum-free medium. It was demonstrated that these effects are independent of the amount of addition of a growth factor that induces the growth of the transformed CHO cells. In this Example, it was demonstrated that no significant difference is observed in the cell count and the total yield of the recombinant protein by transformed CHO cells, even if the amount of addition of a recombinant human insulin is reduced in a serum-free medium containing the insulin as a growth factor which induces the growth of the CHO cells.

The serum-free medium used for the cultivation had the same composition as basal medium composition A shown in Table 3 except for the amount of addition of a recombinant human insulin. To this basal medium, 3 g/liter of soybean protein hydrolysate, 2 g/liter of yeast extract and 1 g/liter of wheat protein hydrolysate were added. A recombinant human insulin was added to the medium at 5 mg/liter, 2.5 mg/liter, 1.25 mg/liter or 0 mg/liter (no addition). The cultivation condition for each case was as described in Example 2 above. At the beginning of cultivation, CHO cells were seeded in each serum-free medium at a density of $3.0 \times 10^5$ cells/ml. These CHO cells were cultured in advance in a serum-free medium (basal medium A supplemented with 3 g/liter of soybean protein hydrolysate, 2 g/liter of yeast extract and 1 g/liter of wheat protein hydrolysate) under the conditions described in Example 2 above.

TABLE 3

Basal Medium Components A

| Component | Amount of Addition (mg/L) |
| --- | --- |
| Sodium Chloride | 1025 |
| Potassium Chloride | 313.8 |
| Glucose (Dextrose) anhyd. | 8000 |
| L-Alanine | 16.955 |
| L-Arginine HCl | 168.845 |
| L-Asparagine $H_2O$ | 32.5 |
| L-Asparatic Acid | 21.655 |
| L-Cysteine HCl $H_2O$ | 128 |
| L-Glutamic Acid | 44.855 |
| L-Glutamine | 1169.2 |
| Glycine | 28.755 |
| L-Histidine HCl $H_2O$ | 31.425 |
| L-Isoleucine | 27.97 |
| L-Leucine | 32.56 |
| L-Lysine HCl | 54.505 |
| L-Methionine | 9.74 |
| L-Phenylalanine | 18.48 |
| L-Proline | 37.265 |
| L-Serine | 17.755 |
| L-Threonine | 29.955 |
| L-Tryptophan | 6.02 |
| L-Tyrosine 2Na $2H_2O$ | 29.865 |

TABLE 3-continued

Basal Medium Components A

| Component | Amount of Addition (mg/L) |
|---|---|
| L-Valine | 28.855 |
| Ascorbic Acid | 25 |
| Folic Acid | 1.16 |
| Inositol | 10.01 |
| Nicotinic Acid Amide | 0.5185 |
| Riboflavin | 0.069 |
| Sodium Selenite | 0.004324 |
| Thiamine HCl | 0.6685 |
| Thioctic Acid, D-L (Liopoic Acid) | 0.203 |
| Cytidine | 5 |
| 2' Deoxyadenosine 1H$_2$O | 5 |
| 2' Deoxycytidine HCl | 5 |
| 2' Deoxyguanosine | 5 |
| Guanosine | 5 |
| Uridine | 5 |
| Adenosine | 5 |
| Pyridoxine HCl | 0.031 |
| Putrescine 2HCl | 0.0805 |
| Cupric Sulfate CuSO$_4$ 5H$_2$O | 0.00125 |
| Ferrous Sulfate FeSO$_4$ 7H$_2$O | 0.417 |
| Zinc Sulfate ZnSO$_4$ 7H$_2$O | 0.4315 |
| d-Biotin | 0.05365 |
| Pantothenic Acid Ca salt | 0.619 |
| Vitamin B12 (aka CYANOCOBALAMIN) | 1.36 |
| Pyridoxal HCl | 0.5 |
| Pyruvic Acid, Na salt | 110 |
| NaH$_2$ PO$_4$ H$_2$O | 70 |
| Na$_2$ HPO$_4$ anhyd. | 82.49 |
| Calcium Chloride anhyd. | 116.65 |
| Magnesium Chloride anhyd. | 28.57 |
| Magnesium Sulfate | 50 |
| Ethanolamine HCl | 1.95 |
| KH$_2$ PO$_4$ 4 | 2 |
| Choline Chloride | 7.48 |
| Pluronic F-68 | 1000 |
| EDTA Ferric-Sodium Salt Dihydrate | 25.0 |
| Insulin Human Recombinant | 5 |
| Sodium Bicarbonate | 1608 |

Figure 7A:
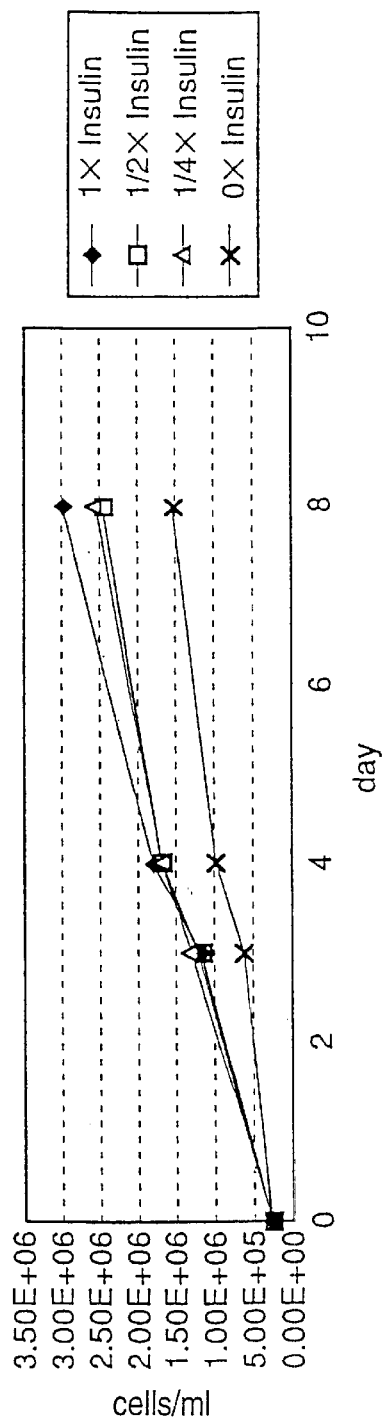
FIGS. 7a and 7b are graphs showing the effect of the amount of addition of insulin on the growth rate of transformed CHO cells when subcultured in the presence of wheat protein hydrolysate in the medium in addition to soybean protein hydrolysate and yeast extract.
Figure 7B:
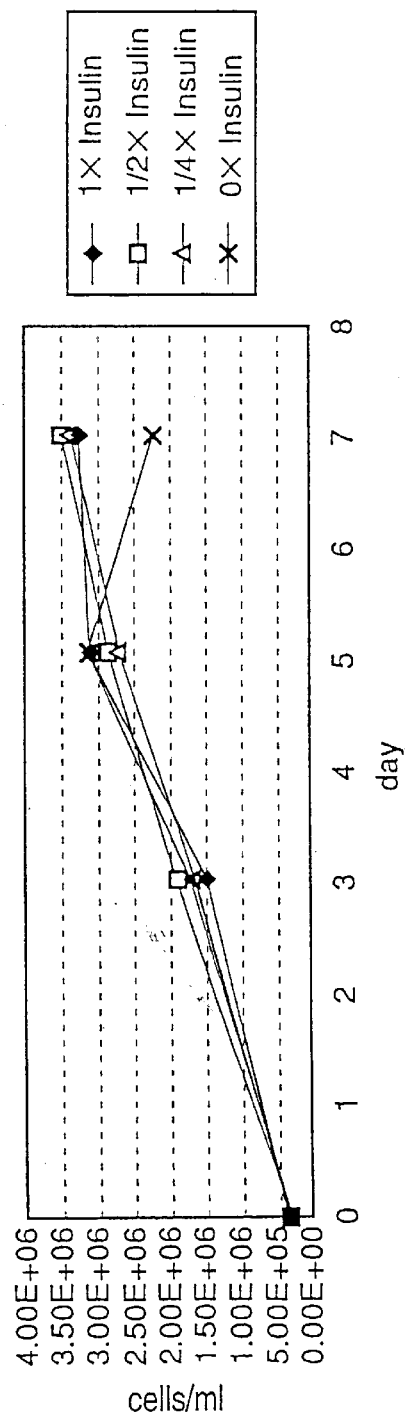

Panel "a" in FIG. 7 shows the time course of the number of cultured cells for 8 days from the beginning of the cultivation, and panel "a" in FIG. 8 shows the time course of the total yield of the recombinant protein produced by the cultured cells during the above period; in each panel, 4 different conditions were used as regards the amount of addition of the recombinant human insulin. Panel "b" in FIG. 7 and panel "b" in FIG. 8 show the further results obtained when the cells cultured for 8 days were subcultured in a fresh medium.

As shown in FIG. 7, even if the amount of addition of the recombinant human insulin is reduced to ¼, no significant difference is observed in the cell count. Also, as shown in FIG. 8, no significant difference is observed in the total yield of the recombinant protein produced by the cultured cells during the same period. Although cell growth is observed under the condition that the recombinant human insulin was added at 0 mg/liter (i.e., no addition), this cell growth is believed to be attributable to the fact that the seeded cells were pre-cultured in a medium containing a recombinant human insulin; this history should have influenced their growth.

When the cells were subcultured in a fresh medium after 8 days from the beginning of the cultivation, results almost similar to the above-described results were obtained. From these results, it is confirmed that the effectiveness in maintaining or increasing the number of cultured cells and inhibiting the decrease in cell viability (as achieved by adding wheat protein hydrolysate, as well as soybean protein hydrolysate and yeast extract to the medium) is maintained in the cells when they are subcultured in a fresh medium.

It was found that since stable cell growth can be achieved by adding wheat protein hydrolysate, as well as soybean protein hydrolysate and yeast extract to the medium, cell growth of good reproducibility can be achieved even if the amount of addition of the growth factor necessary for inducing the growth of CHO cells under a condition of low cell density following subculture in a fresh medium is varied to some extent. Specifically, when a recombinant human insulin is used as the growth factor, it may safely be concluded that the cultivation efficiency per se will not be influenced by ranging the amount of addition of the insulin within the range of 1.25–5 mg/liter, preferably 2–5 mg/liter. Furthermore, since cell viability can be maintained at high level by adding to wheat protein hydrolysate, as well as soybean protein hydrolysate and yeast extract to the medium, cultivation efficiency is stabilized in each generation of subculture, and yet the total yield of the recombinant protein produced by the cultured cells is also stabilized.

EXAMPLE 4

Substitution of Glucose with Fructose

In the serum-free medium of the invention, monosaccharides which are common energy sources are used. In this Example, it was demonstrated that fructose can be used instead of glucose.

In the serum-free medium of Example 2 which was obtained by adding 3 g/liter of soybean protein hydrolysate, 2 g/liter of yeast extract and 1 g/liter of wheat protein hydrolysate to the basal medium shown in Table 2, 8 g/liter of glucose was replaced with 1.6 g/liter of glucose and 6.4 g/liter of fructose. In addition to the initial medium containing 8 g/liter of glucose and the newly prepared medium containing 1.6 g/liter of glucose and 6.4 g/liter of fructose, two other media were prepared by increasing the amount of addition of the recombinant human insulin in the said respective media from 5 mg/liter to 10 mg/liter. Using these 4 types of serum-free media, transformed CHO cells were cultured. Cultivation conditions were as follows. Thirty milliliters of the medium was placed in a 125-ml flask. Cells were seeded at a density of $3.0 \times 10^5$ cells/ml and cultured under agitation at 160 rpm, at 37° C., under 5% $CO_2$.

Figure 10:
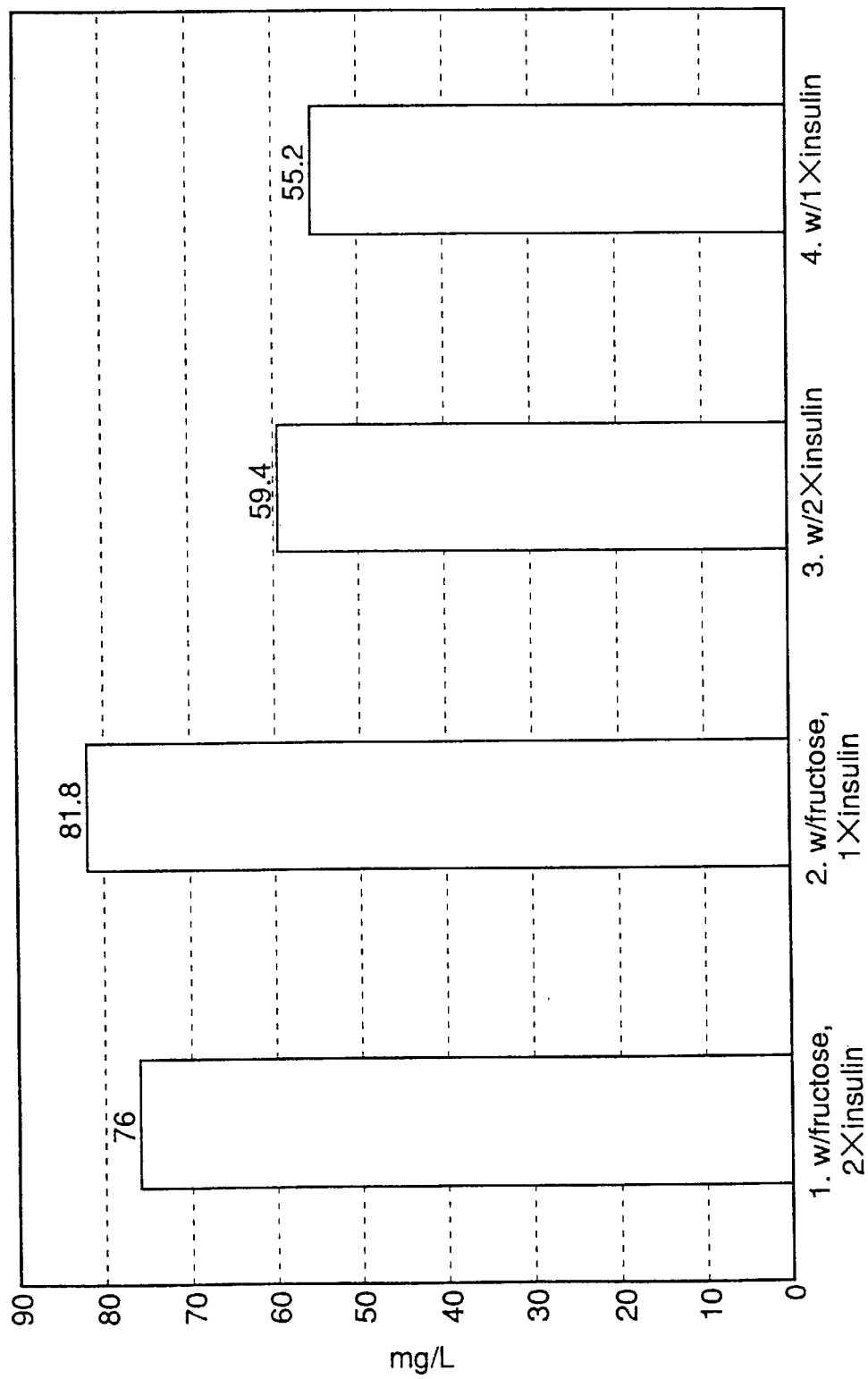
FIG. 10 is a graph comparing the yields of a recombinant protein by transformed CHO cells when the glucose contained in the medium is replaced with fructose for culturing in the presence of wheat protein hydrolysate in the medium in addition to soybean protein hydrolysate and yeast extract.

The cell count and the viability of the cultured cells on day 4 of the cultivation and thereafter, and the total yield of the recombinant protein by the transformed CHO cells up to day 7 of the cultivation were measured to evaluate the influence of increasing the amount of addition of the recombinant human insulin from 5 mg/liter to 10 mg/liter and the influence of replacing glucose with fructose as a monosaccharide. FIG. 9 shows the results of comparison of viabilities on day 4 of the cultivation and thereafter. FIG. 10 shows the results of comparison of the total yields of the recombinant protein by the transformed CHO cells up to day 7 of the cultivation. As shown in FIG. 10, when the amount of addition of the recombinant human insulin was increased, the cultivation rate increased to some extent and, as a result, some increase was observed in the total yield of the recombinant protein produced by the cultured cells. In addition, it was confirmed that the substitution of fructose for glucose significantly increases the yield of the recombinant protein. It may safely be concluded that this effect of substitution of fructose for glucose is achieved independently of the amount of addition of the recombinant human insulin.

By contrast, as shown in FIG. 9, it was found that the viability of the cultured cells on day 4 of the cultivation and thereafter significantly decreases as a result of the substitution of fructose for glucose. It was found that this decrease in the viability of the cultured cells occurred concomitantly with the increase in the total yield of the recombinant protein by the transformed CHO cells. Further, it was confirmed separately that as the ratio of substitution of fructose for glucose increases, the above-mentioned influence increases in proportion. From these results, it was confirmed that the viability of cultured cells can be maintained at 20% or highed by adjusting the ratio of substitution of fructose for glucose to less than 80%, although the decrease in the viability of cultured cells is not necessarily desirable when transformed CHO cells are subcultured in a fresh medium for continuous production of a recombinant protein. As long as the viability of the cultured cells is maintained at 20% or higher, it may safely be concluded that the decrease in viability will not give an extremely bad influence and will not lead to an overall decrease in productivity in the continuous production of a recombinant protein by subculture.

In other words, it was confirmed that by utilizing the inhibitory action of wheat protein hydrolysate against the decrease in the viability of cultured cells, a production efficiency practically comparable to that achieved using a medium containing glucose as an energy source can be achieved with a medium in which glucose is replaced by fructose for continuous production of a recombinant protein by subculture.

EXAMPLE 5

Comparison with a Serum-Free Medium Containing Animal-Derived Proteins

The serum-free medium of the invention was compared with a serum-free medium containing animal-derived proteins which is obtained by replacing the three characteristic components of the serum-free medium of the invention (i.e., soybean protein hydrolysate, yeast extract and wheat protein hydrolysate) with animal-derived proteins that are commonly used as additives to a serum-free medium. It was demonstrated that there is no significant difference between these two serum-free media in cultivation results, and that the addition of the above three characteristic components in the serum-free medium of the invention produces a superior or at least equivalent effect compared to the addition of animal-derived proteins which are commonly used additives.

Specifically, as a serum-free medium containing animal-derived proteins, basal medium C shown in Table 4 below and supplemented with bovine serum albumin, bovine fetuin and primatone (beef hydrolysate) was used. The bovine serum albumin used was a commercial product verified to be free of contamination with virus and others after inspection of contaminants such s virus. The bovine fetuin and the primatone used were also commercial products verified to be free of contamination with virus and others after inspection of contaminants such as virus. The amounts of addition of the respective animal-derived proteins per liter of the medium were as follows: bovine serum albumin (virus free) 100 mg, fetuin 200 mg, human transferrin 5 mg and primatone 2500 mg.

TABLE 4

Basal Medium Components C

| Component | Amount of Addition (mg/L) |
|---|---|
| Sodium Chloride | 6867 |
| Potassium Chloride | 313.8 |
| Glucose (Dextrose) anhyd. | 3401 |
| L-Alanine | 16.955 |
| L-Arginine HCl | 168.845 |
| L-Asparagine H$_2$O | 32.5 |
| L-Asparatic Acid | 21.655 |
| L-Cysteine HCl H$_2$O | 67.565 |
| L-Cystine 2Na Salt | 14.195 |
| L-Glutamic Acid | 44.855 |
| L-Glutamine | 876 |
| Glycine | 28.755 |
| L-Histidine HCl H$_2$O | 31.425 |
| L-Isoleucine | 27.97 |
| L-Leucine | 32.56 |
| L-Lysine HCl | 54.505 |
| L-Methionine | 9.74 |
| L-Phenylalanine | 18.48 |
| L-Proline | 37.265 |
| L-Serine | 17.755 |
| L-Threonine | 29.955 |
| L-Tryptophan | 6.02 |
| L-Tyrosine 2Na 2H$_2$O | 29.865 |
| L-Valine | 28.855 |
| Ascorbic Acid | 25 |
| Folic Acid | 1.16 |
| Inositol | 10.01 |
| Nicotinic Acid Amide | 0.5 |
| Riboflavin | 0.05 |
| Sodium Selenite | 0.004324 |
| Thiamine HCl | 0.5 |
| Thioctic Acid, D-L (Liopoic Acid) | 0.10 |
| Cytidine | 5 |
| 2' Deoxyadenosine 1H$_2$O | 5 |
| 2' Deoxycytidine HCl | 5 |
| 2' Deoxyguanosine | 5 |
| Guanosine | 5 |
| Uridine | 5 |
| Adenosine | 5 |
| Pyridoxine HCl | 0.031 |
| Putrescine 2HCl | 0.0805 |
| Cupric Sulfate CuSO$_4$ 5H$_2$O | 0.00125 |
| Ferrous Sulfate FeSO$_4$ 7H$_2$O | 0.417 |
| Zinc Sulfate ZnSO$_4$ 7H$_2$O | 0.4315 |
| d-Biotin | 0.05 |
| Pantothenic Acid Ca salt | 0.5 |
| Vitamin B12 (aka CYANOCOBALAMIN) | 1.36 |
| Pyridoxal HCl | 0.5 |
| Pyruvic Acid, Na salt | 110 |
| NaH$_2$ PO$_4$ H$_2$O | 70 |
| Na$_2$ HPO$_4$ anhyd. | 82.49 |
| Calcium Chloride anhyd. | 116.65 |
| Magnesium Chloride anhyd. | 28.57 |
| Magnesium Sulfate anhyd. | 50 |
| Ethanolamine HCl | 1.95 |
| KH$_2$ PO$_4$ | 2.0 |
| Choline Chloride | 7.48 |
| Pluronic F-68 | 1000 |
| Insulin (Bovine) | 5 |
| Sodium Bicarbonate | 1608 |

In Table 4 above, an iron-EDTA complex is also used as an iron source in addition to an inorganic iron salt. The amount of addition of this complex represents the final concentration in the medium when the preparation of the medium has been completed.

The serum-free medium containing the three components, soybean protein hydrolysate, yeast extract and wheat protein hydrolysate, is basal medium A shown in Table 1 and supplemented with 3 g/liter of soybean protein hydrolysate, 2 g/liter of yeast extract and 1 g/liter of wheat protein hydrolysate. Further, as in Example 4, 8000 mg/liter of glucose in the composition of Table 1 was replaced with 1400 mg/liter of glucose and 6600 mg/liter of fructose. To the resultant basal medium, 3 g/liter of soybean protein hydrolysate, 2 g/liter of yeast extract and 1 g/liter of wheat protein hydrolysate were added, and the resultant medium was used for comparison. In addition, another medium was prepared by eliminating only glutamine from the above-mentioned fructose-containing medium and used for comparison. Using these 4 types of serum-free media, transformed CHO cells were cultured. Cultivation conditions were as follows. Thirty milliliters of the medium was placed in a 125 ml flask. Cells were seeded at a density of $3.0 \times 10^5$ cells/ml and cultured under agitation at 160 rpm, at 37° C., under 5% $CO_2$.

Figure 11:
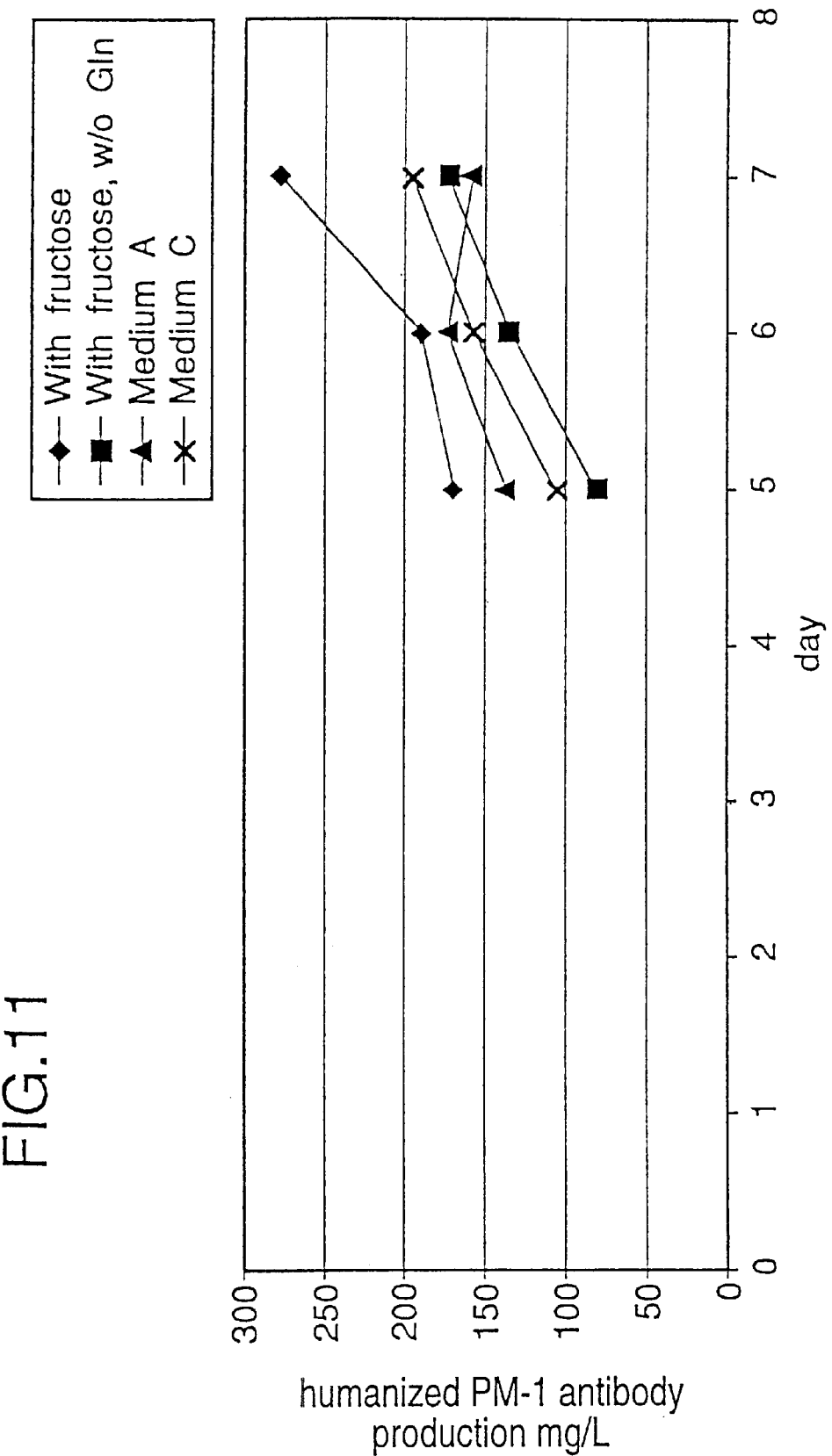
FIG. 11 is a graph comparing the addition of three components, soybean protein hydrolysate, yeast extract and wheat protein hydrolysate, with the addition of animal-derived proteins, bovine serum albumin, fetuin, human transferrin and primatone, as to the effect on the yield of a recombinant protein by transformed CHO cells.
Figure 12:
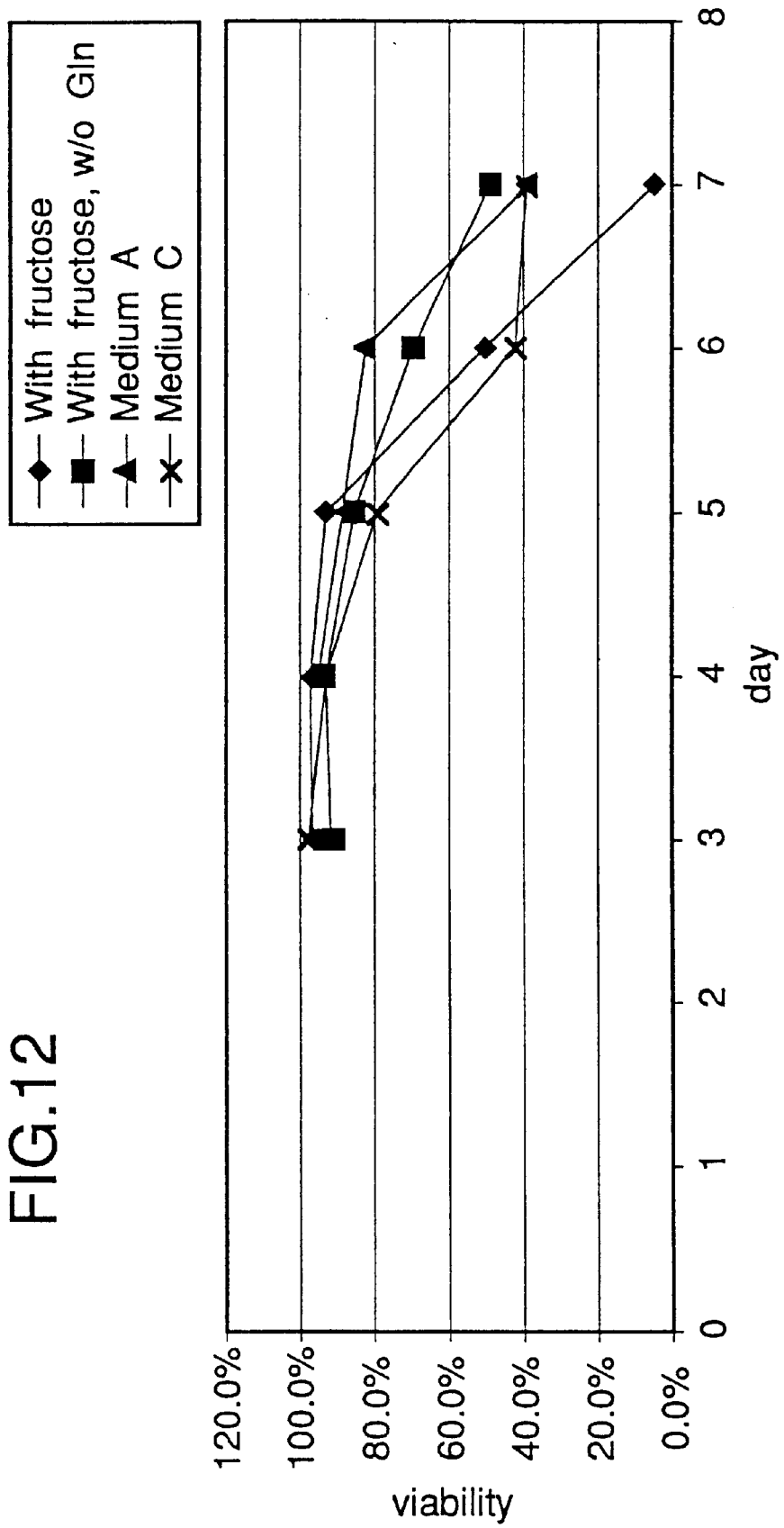
FIG. 12 is a graph comparing the addition of three components, soybean protein hydrolysate, yeast extract and wheat protein hydrolysate, with the addition of animal-derived proteins, bovine serum albumin, fetuin, human transferrin and primatone, as to the effect on the viability of transformed CHO cells.
Figure 13:
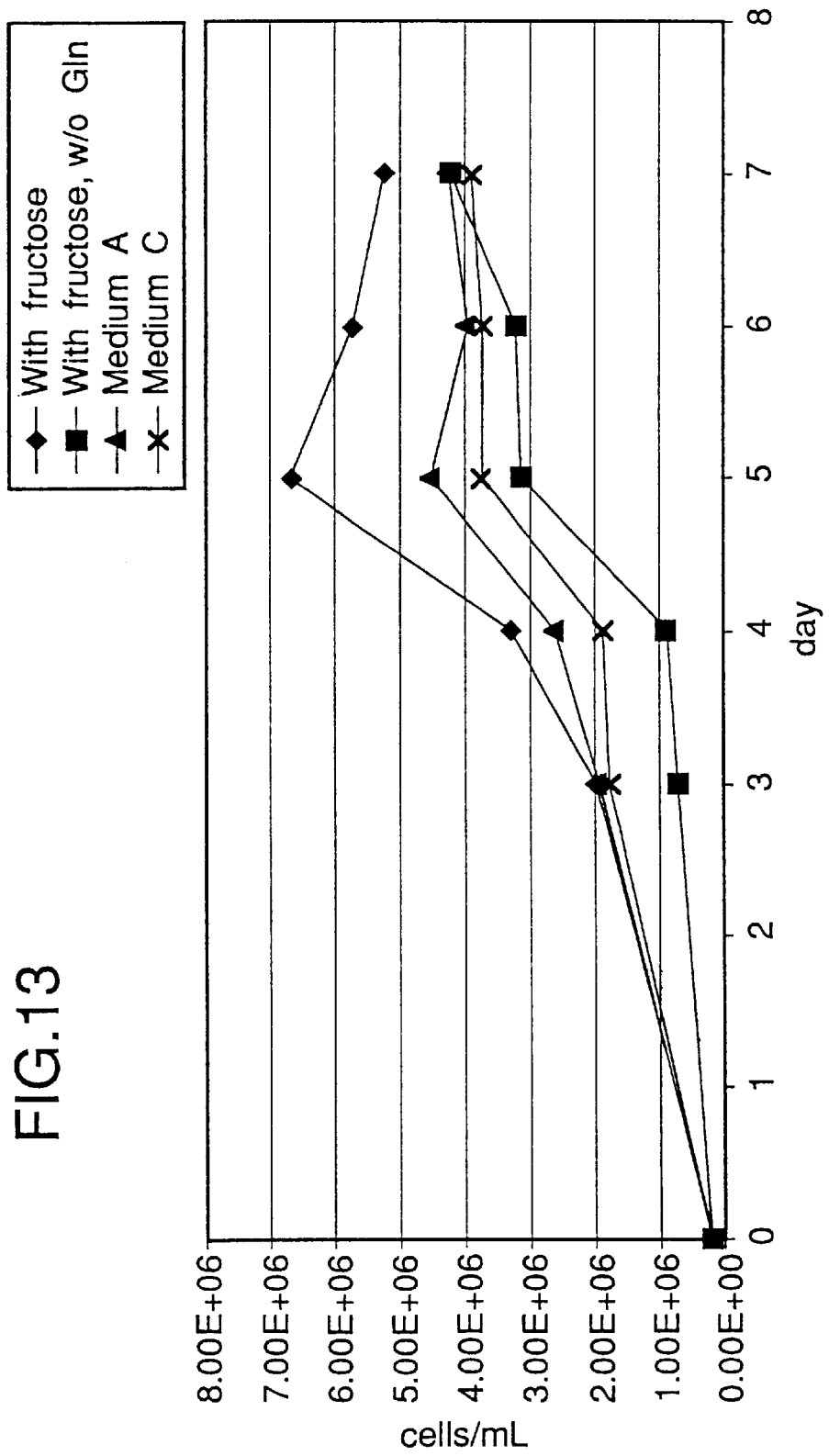
FIG. 13 is a graph comparing the addition of three components, soybean protein hydrolysate, yeast extract and wheat protein hydrolysate, with the addition of animal-derived proteins, bovine serum albumin, fetuin, human transferrin and primatone, as to the effect on the growth rate of transformed CHO cells.

The results obtained, i.e., the cell count on day 3 of the cultivation and thereafter, the cell viability from day 3 to day 7, and the total yield of the recombinant protein accumulated in the medium up to day 7 are shown in FIGS. 11, 12 and 13, respectively.

As shown in FIG. 13, there is no significant difference in the cell count on day 3 between the serum-free medium containing animal-derived proteins and the serum-free medium containing the three components, soybean protein hydrolysate, yeast extract and wheat protein hydrolysate. After the 3rd day of cultivation, the results on cell count were also good in each medium, except for the influence of the substitution of fructose for glucose as shown in Example 4.

What is worth particular mention is the comparison between the serum-free medium containing animal-derived proteins and the serum-free medium which is the basal medium of Table 1 plus the three components, soybean protein hydrolysate, yeast extract and wheat protein hydrolysate; as shown in FIG. 11, the two serum-free media exhibited comparable results as regards the total yield of the recombinant protein accumulated in the medium up to day 7. Similarly, there is only a small difference between these two media in cell viability from day 3 to day 7 of the cultivation, as shown in FIG. 12. That is, the serum-free medium containing the three components, soybean protein hydrolysate, yeast extract and wheat protein hydrolysate produces favorable results almost equal to those produced by the serum-free medium containing three animal-derived proteins, bovine serum albumin, bovine fetuin and primatone (beef hydrolysate), in terms of cultivation rate and production yield of the recombinant protein.

From the above experimental results, the following can be said. The serum-free medium of the invention which is obtained by adding soybean protein hydrolysate and yeast extract to a basal medium containing no components separated from animals promotes and stabilizes the cell growth of transformed CHO cells or the like as induced by a recombinant growth factor added to the serum-free medium, whereby the cultivation rate can be maintained at high level. Further, the serum-free medium of the invention can increase the yield of a recombinant protein produced by the cultured cells. Still further, the serum-free medium of the invention has the advantage that by adding wheat protein hydrolysate, as well as soybean protein hydrolysate and yeast extract, the cell viability can be maintained at high level so that when the cultured cells are subcultured, the cultivation efficiency and the total yield of the recombinant protein produced by the cultured cells are stabilized in each generation. Therefore, utilizing these advantages, a recombinant protein of interest can be produced consistently at high efficiency and with good reproducibility by applying the method of growing transformed animal cells in the serum-free medium of the invention.

What is claimed is:

1. A serum-free medium for culturing animal cells (A) that contains soybean protein hydrolysate, yeast extract and wheat protein hydrolysate and (B) that promotes production of a recombinant protein or peptide.

2. The serum-free medium of claim 1, wherein said medium contains no components which have been separated from animals.

3. The serum-free medium of claim 1, wherein the soybean protein hydrolysate is added at 1–5 g per liter of said medium and the yeast extract is added at 1–5 g per liter of said medium.

4. The serum-free medium of claim 1, wherein the wheat protein hydrolysate is added at 0.5–3 g per liter of said medium.

5. The serum-free medium of claim 3, wherein the ratio by weight of the amount of addition of the soybean protein hydrolysate to the amount of addition of the yeast extract is in the range from 80:20 to 60:40.

6. The serum-free medium of claim 1, wherein the amount of addition of the wheat protein hydrolysate comes within the range from 5 to 60% of the total weight of the soybean protein hydrolysate and the yeast extract added.

7. The serum-free medium of claim 1, wherein said animal cells are transformed cells into which a foreign gene has been transferred.

8. The serum-free medium of claim 1, wherein said animal cells are mammalian cells.

9. The serum-free medium of claim 8, wherein said mammalian cells are Chinese hamster ovary cells.

10. A method for culturing animals cells which comprises culturing animal cells in a serum-free medium (A) that contains soybean protein hydrolysate, yeast extract and wheat protein hydrolysate, and (B) that promotes production of a recombinant protein or peptide.

11. The method of claim 10, wherein said animal cells are transformed cells into which a foreign gene has been transferred.

12. The method of claim 10, wherein said animal cells are mammalian cells.

13. The method of claim 12, wherein said mammalian cells are Chinese hamster ovary cells.

14. A method for producing a substance which comprises
(1) culturing animal cells in a serum-free medium (A) that contains soybean protein hydrolysate, yeast extract and wheat protein hydrolysate, and (B) that promotes production of a recombinant protein or peptide, causing said substance to be produced by and secreted out of said animals cells, and
(2) isolating said substance from said serum-free medium.

15. The method of claim 14, wherein said substance is a protein or peptide.

16. The method of claim 14, wherein said animal cells are transformed cells into which a foreign gene has been transferred and said substance produced by and secreted out of said animal cells is a gene product of the transferred foreign gene.

17. The method of claim 16, wherein said gene product is a recombinant protein or peptide.

18. The method of claim 14, wherein said animal cells are mammalian cells.

19. The method of claim 18, wherein said mammalian cells are Chinese hamster ovary cells.

20. A serum-free medium for culturing animal cells that contains soybean protein hydrolysate, wheat protein hydrolysate and yeast extract, wherein the ratio by weight of the amount of added soybean protein hydrolysate to the ratio by weight of the amount of added yeast extract is in the range of 50:50 to 90:10.

* * * * *